US007497828B1

(12) United States Patent
Wilk et al.

(10) Patent No.: US 7,497,828 B1
(45) Date of Patent: *Mar. 3, 2009

(54) ULTRASONIC MEDICAL DEVICE AND ASSOCIATED METHOD

(75) Inventors: Peter J. Wilk, New York, NY (US); Timothy J. Nohara, Fonthill (CA); Peter T. Weber, Dundas (CA)

(73) Assignee: Wilk Ultrasound of Canada, Inc., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/514,928

(22) Filed: Feb. 28, 2000

Related U.S. Application Data

(63) Continuation-in-part of application No. 09/153,451, filed on Sep. 15, 1998, now Pat. No. 6,306,090, which is a continuation of application No. 08/839,971, filed on Apr. 24, 1997, now Pat. No. 5,871,446, which is a continuation-in-part of application No. 08/510,104, filed on Aug. 1, 1995, now Pat. No. 5,666,953, which is a division of application No. 07/819,120, filed on Jan. 10, 1992, now Pat. No. 5,437,278, application No. 09/514,928, which is a continuation of application No. 08/892,955, filed on Jul. 16, 1997, now Pat. No. 6,023,632.

(51) Int. Cl.
*A61B 8/00* (2006.01)

(52) U.S. Cl. ...................................... 600/443
(58) Field of Classification Search .......... 600/443–448, 600/454–456, 442, 460, 459, 437; 128/916; 73/625–626, 628
See application file for complete search history.

(56) References Cited

U.S. PATENT DOCUMENTS 3,552,382 A 1/1971 Mount (Continued)

OTHER PUBLICATIONS

Li, P. et al "Phase Aberration Correction on Two–Dimensional Conformal Arrays", IEEE Trans UFFC V42#1 Jan. 1995 pp. 73–82.*

(Continued)

*Primary Examiner*—Francis J. Jaworski
(74) *Attorney, Agent, or Firm*—R. Neil Sudol; Henry D. Coleman; William J. Sapone

(57) ABSTRACT

A medical system includes a carrier and a multiplicity of electromechanical transducers mounted to the carrier, the transducers being disposable in effective pressure-wave-transmitting contact with a patient. Energization componentry is operatively connected to a first plurality of the transducers for supplying the same with electrical signals of at least one pre-established ultrasonic frequency to produce first pressure waves in the patient. A control unit is operatively connected to the energization componentry and includes an electronic analyzer operatively connected to a second plurality of the transducers for performing electronic 3D volumetric data acquisition and imaging (which includes determining three-dimensional shapes) of internal tissue structures of the patient by analyzing signals generated by the second plurality of the transducers in response to second pressure waves produced at the internal tissue structures in response to the first pressure waves. The control unit includes phased-array signal processing circuitry for effectuating an electronic scanning of the internal tissue structures which facilitates one-dimensional (vector), 2D (planar), and 3D (volume) data acquisition. The control unit further includes circuitry for defining multiple data gathering apertures and for coherently combining structural data from the respective apertures to increase spatial resolution. When the data gathering apertures are contained in a flexible web or carrier so that the instantaneous positions of the data gathering apertures are unknown, a self-cohering algorithm is used to determine their positions so that coherent aperture combining can be performed.

7 Claims, 15 Drawing Sheets

U.S. PATENT DOCUMENTS

| | | | |
|---|---|---|---|
| 3,805,596 A * | 4/1974 | Klahr | 73/602 |
| 3,927,662 A | 12/1975 | Ziedonis | |
| 4,048,616 A | 9/1977 | Hart et al. | |
| 4,149,420 A | 4/1979 | Hutchison et al. | |
| 4,315,514 A | 2/1982 | Drewes et al. | |
| 4,395,909 A * | 8/1983 | Steinberg et al. | 73/602 |
| 4,434,661 A * | 3/1984 | Miwa et al. | 73/625 |
| 4,446,740 A | 5/1984 | Wilson et al. | |
| 4,623,219 A | 11/1986 | Trias | |
| 4,646,158 A | 2/1987 | Ohno et al. | |
| 4,671,293 A * | 6/1987 | Shaulov | 600/447 |
| 4,757,820 A | 7/1988 | Itoh | |
| 4,771,786 A | 9/1988 | Iinuma | |
| 4,819,649 A | 4/1989 | Rogers et al. | |
| 4,991,604 A | 2/1991 | Wurster et al. | |
| 5,078,143 A | 1/1992 | Okazaki et al. | |
| 5,091,893 A | 2/1992 | Smith et al. | |
| 5,099,459 A | 3/1992 | Smith | |
| 5,099,848 A | 3/1992 | Parker et al. | |
| 5,113,706 A * | 5/1992 | Pittaro | 73/626 |
| 5,135,001 A | 8/1992 | Sinofsky et al. | |
| 5,152,294 A * | 10/1992 | Mochizuki et al. | 600/459 |
| 5,163,436 A | 11/1992 | Saitoh et al. | |
| 5,167,231 A | 12/1992 | Matsui | |
| 5,203,336 A | 4/1993 | Iida et al. | |
| 5,235,986 A | 8/1993 | Maslak et al. | |
| 5,375,470 A * | 12/1994 | Matsushima et al. | 73/626 |
| 5,391,140 A | 2/1995 | Schaetzle et al. | |
| 5,394,877 A | 3/1995 | Orr et al. | |
| 5,435,311 A | 7/1995 | Umemura et al. | |
| 5,437,278 A | 8/1995 | Wilk | |
| 5,448,994 A | 9/1995 | Iinuma | |
| 5,488,952 A | 2/1996 | Schoolman | |
| 5,526,815 A | 6/1996 | Granz et al. | |
| 5,611,343 A | 3/1997 | Wilson | |
| 5,611,345 A | 3/1997 | Hibbeln | |
| 5,619,999 A | 4/1997 | Von Behren et al. | |
| 5,666,953 A | 9/1997 | Wilk | |
| 5,680,863 A * | 10/1997 | Hossack et al. | 600/459 |
| 5,752,518 A * | 5/1998 | McGee et al. | 600/424 |
| 5,793,701 A * | 8/1998 | Wright et al. | 367/7 |
| 5,871,446 A * | 2/1999 | Wilk | 600/407 |
| 5,984,882 A | 11/1999 | Rosenschein et al. | |
| 5,997,479 A | 12/1999 | Savord et al. | |
| 6,023,632 A | 2/2000 | Wilk | |
| 6,106,463 A * | 8/2000 | Wilk | 600/437 |
| 6,106,471 A | 8/2000 | Wiesauer et al. | |
| 6,129,672 A | 10/2000 | Seward et al. | |
| 6,135,960 A * | 10/2000 | Holmberg | 600/447 |
| 6,155,978 A | 12/2000 | Cline et al. | |
| 6,159,153 A * | 12/2000 | Dubberstein et al. | 600/443 |
| 6,186,948 B1 * | 2/2001 | Kamiyama et al. | 600/443 |
| 6,213,947 B1 * | 4/2001 | Phillips | 600/443 |
| 6,213,948 B1 * | 4/2001 | Barthe et al. | 600/445 |
| 6,238,346 B1 | 5/2001 | Mason | |
| 6,276,211 B1 * | 8/2001 | Smith | 73/626 |
| 6,419,633 B1 * | 7/2002 | Robinson et al. | 600/443 |
| 6,482,160 B1 | 11/2002 | Stergiopoulos et al. | |
| 6,503,204 B1 * | 1/2003 | Sumanaweera et al. | 600/459 |

OTHER PUBLICATIONS

"Elevation Performance of 1.25D and 1.5D Transducer Arrays," Wildes, D.G. et al., IEEE Transactions on Ultrasound, Ferroelectronics and Frequency Control, vol. 44, No. 5, Sep. 1997, pp. 1027–1036.

"Elevation Beamforming Performance of a 1.75D Array," Guo, Puyun et al., IEEE Ultrasound, Ferroelectronics and Frequency Control.

* cited by examiner

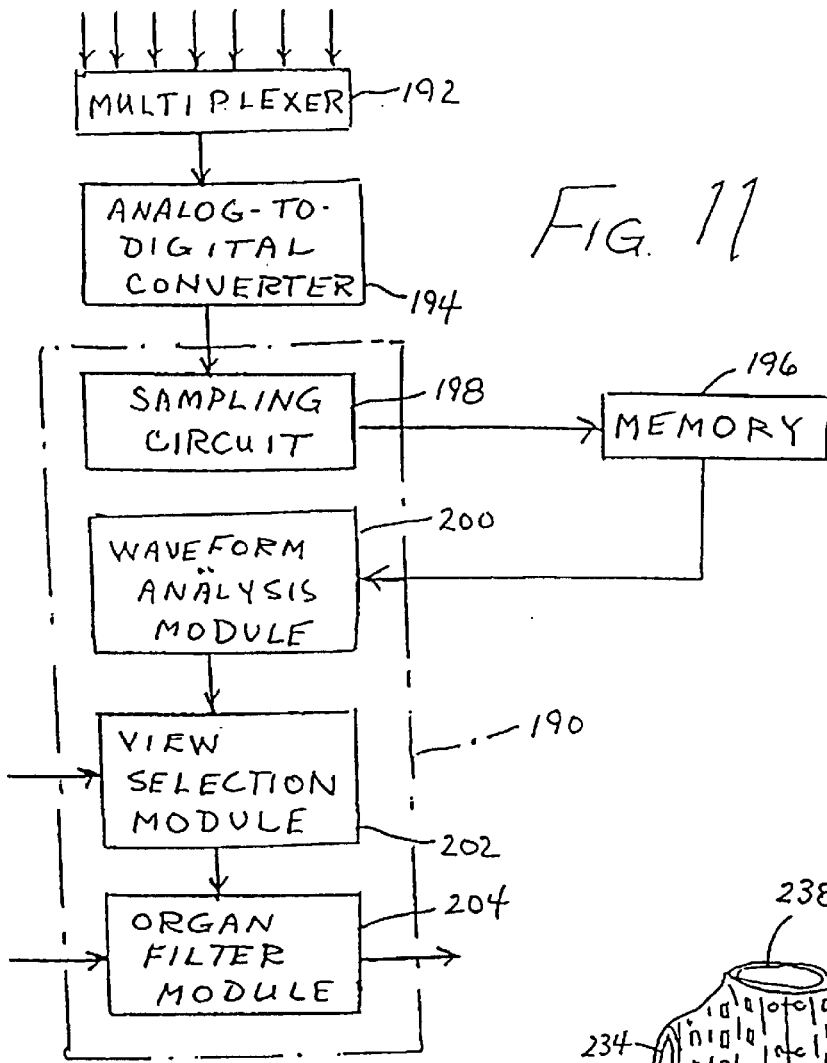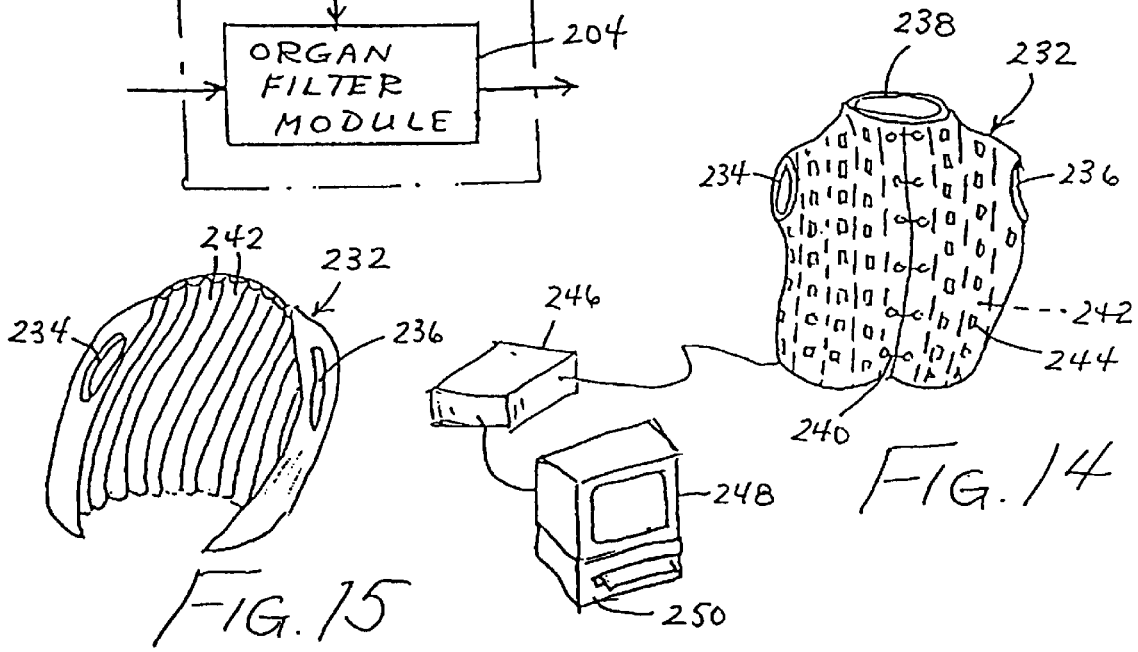

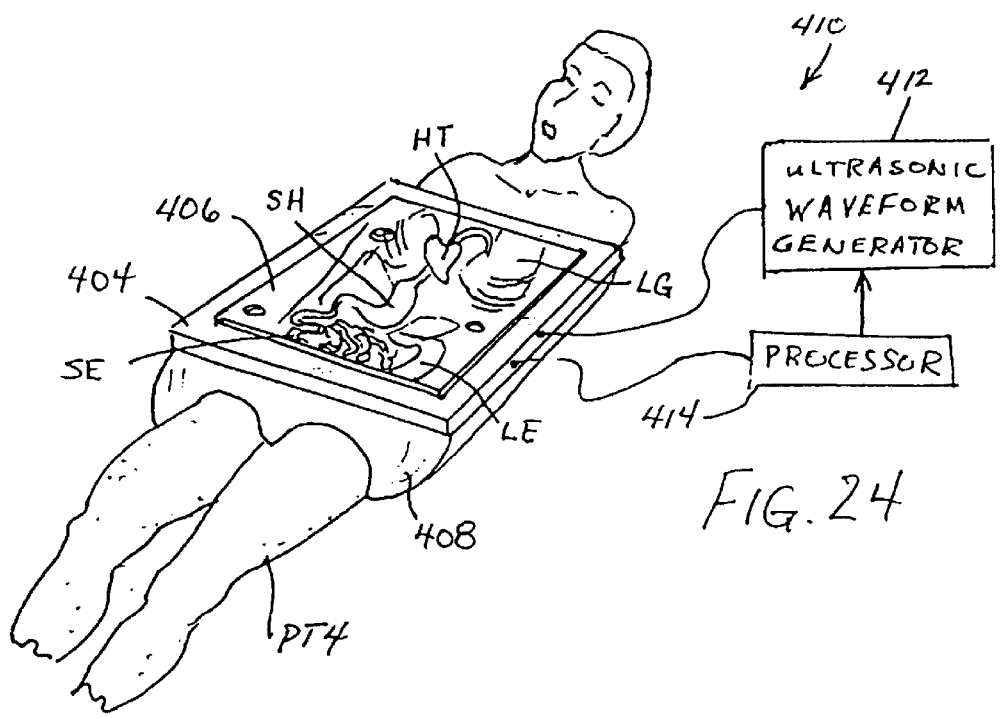
FIG. 24
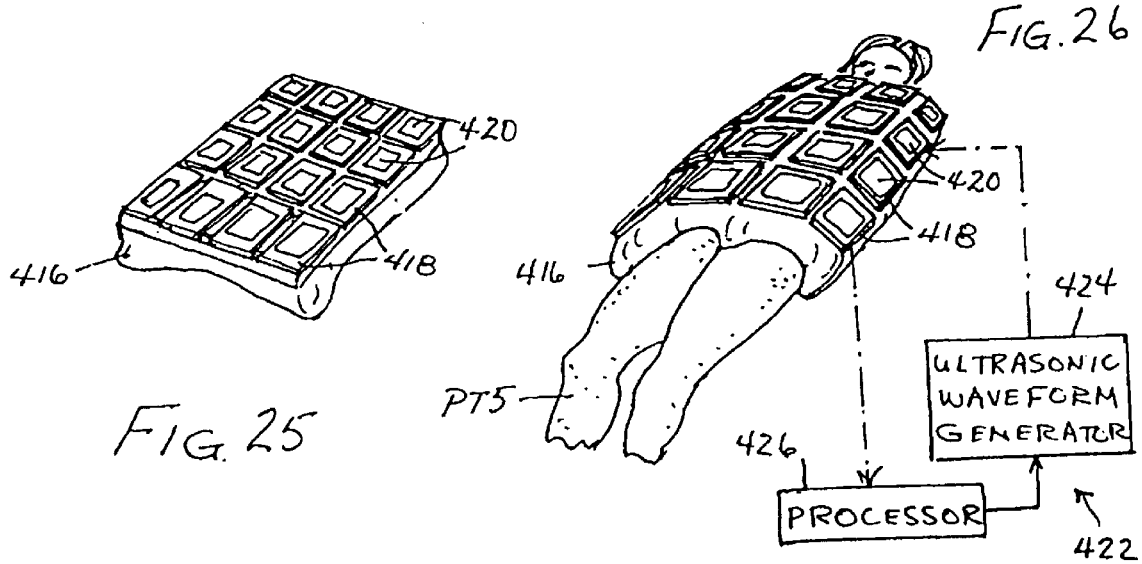
FIG. 25
FIG. 26

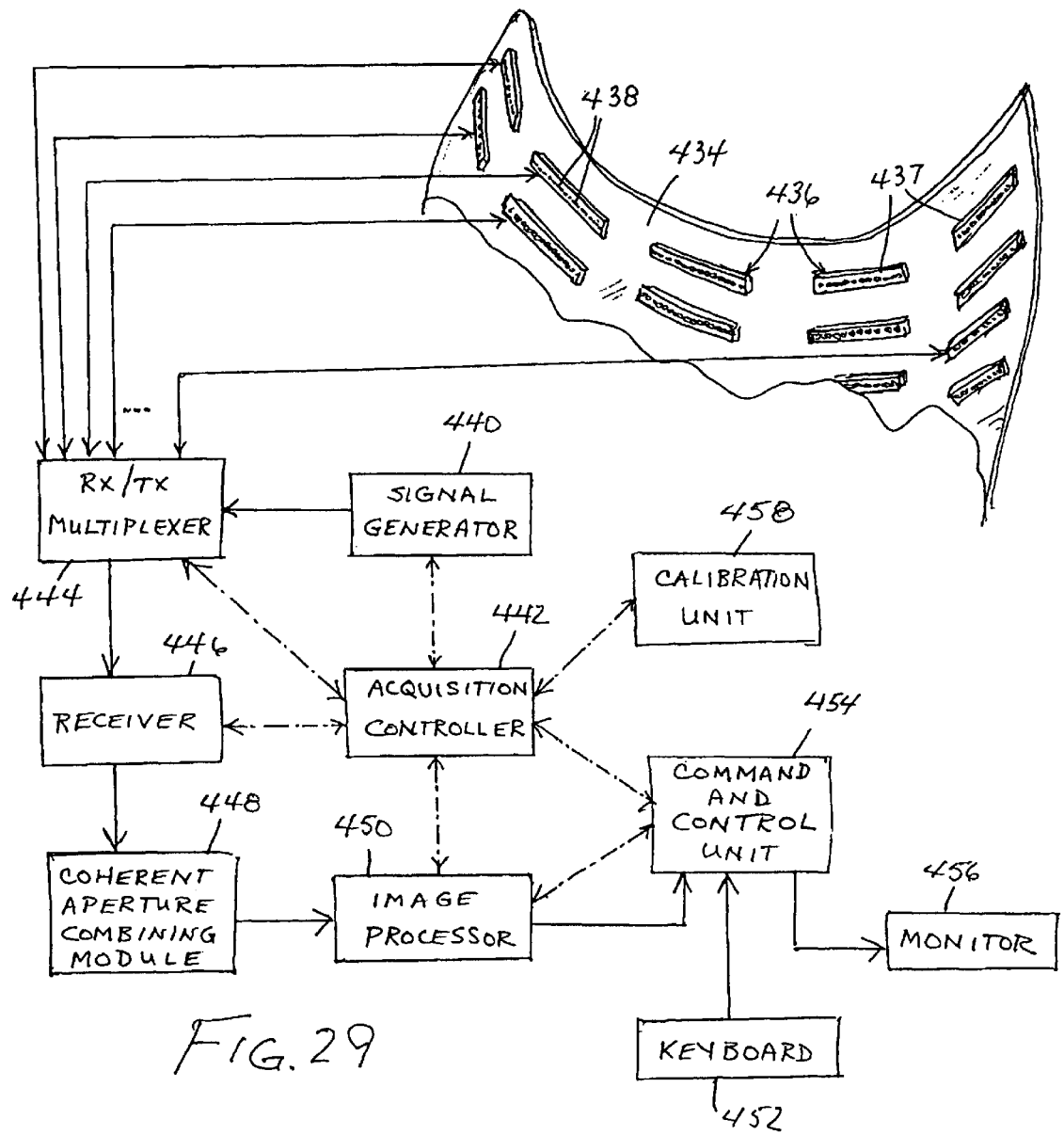

ULTRASONIC MEDICAL DEVICE AND ASSOCIATED METHOD

CROSS-REFERENCE TO RELATED APPLICATIONS

This application is a continuation-in-part of application Ser. No. 09/153,451 filed Sep. 15, 1998, now U.S. Pat. No. 6,306,090. Application Ser. No. 09/153,451 was filed as a continuation of application Ser. No. 08/839,971 filed Apr. 24, 1997, now U.S. Pat. No. 5,871,446, which was filed as a continuation in part and a division of application Ser. No. 08/510,104 filed Aug. 1, 1995 now U.S. Pat. No. 5,666,953. Application Ser. No. 08/510,104 was in turn filed as a division of application Ser. No. 07/819,120 filed Jan. 10, 1992, now U.S. Pat. No. 5,437,278. This application is also a continuation of application Ser. No. 08/892,955 filed Jul, 16, 1997 now U.S. Pat. No. 6,023,632.

BACKGROUND OF THE INVENTION

This invention relates to a device or system for use in medical diagnoses and treatment. The device or system is especially useful for medical imaging purposes to enable a visual inspection of internal tissue structures.

In recent years, the escalation of medical costs has captured substantial media and regulatory attention. One reason for the escalating costs is the ever increasing use of expensive machines and testing techniques. Computed assisted tomography (CAT scanning), magnetic resonance imaging (MRI) and some radiological techniques have been in the forefront of contributing to mounting medical costs. In addition to being expensive, these devices are heavy and bulky, making them ill suited to transport.

In this age of rapidly escalating medical costs, minimally invasive operations have become the method of choice for diagnosis and treatment. In many cases, endoscopic, laparoscopic and radiographic techniques have superseded older diagnostic and therapeutic surgical techniques.

Ultrasonic imaging tools are not uncommon in medical offices. These existing devices invariably include a probe provided at a distal or free end with an ultrasonic transducer. The operator moves the probe over a skin surface of a patient while viewing images generated on a video monitor. Upon detecting an image containing information of interest, the operator presses a button to record the image.

The images produced during a conventional ultrasonic scanning procedure are not easily decipherable. Even physicians intimately familiar with internal tissue structures of human beings find it difficult to read conventional ultrasonically generated images without substantial training.

Conventional ultrasound images are two-dimensional (2D) and represent a cross-sectional cut or plane through internal tissues. The data needed for these 2D images are acquired electronically using the probe. The probe scans electronically in a single lateral or length dimension to scan a beam and hence is referred to as a one-dimensional (1D) transducer array; and the second dimension in a 2D image is the range or depth dimension (i.e. into the body). Interest in three-dimensional (3D) ultrasound imaging is increasing rapidly, notwithstanding the fact that presently, it is not possible to obtain electronic 3D volumetric data acquisition. Electronic 3D volumetric data acquisition requires a probe that can electronically scan in a width dimension as well as a length dimension (i.e. the probe must incorporate a 2D transducer array). Such probes are not currently available, and are not expected to be in the near future due to multiplicative complexities known to those skilled in the art in implementing a 2D transducer array, However, 1.5D transducer arrays are available. These arrays scan only in one dimension (i.e. the length dimension) as the 1D transducer arrays; however, they include a few additional rows of transducer elements in the width dimension giving the appearance of a rectangular 2D array. The purpose of the few additional rows (where each row is effectively a 1D array consisting typically of approximately 100 transducer elements) of elements is to provide better focus in the width dimension as a function of depth.

OBJECTS OF THE INVENTION

An object of the present invention is to provide an imaging device or system which is relatively inexpensive and easy to transport.

It is another object of the present invention to provide an alternative to conventional medical imaging systems.

A further object of the present invention is to provide a medical imaging system which exhibits reduced costs over conventional imaging systems such as CAT scanners and MRI machines.

A particular object of the present invention is to provide a medical imaging system which can be used during the performance of so-called minimally invasive medical operations.

It is an additional object of the present invention to provide a medical imaging system which is portable.

Another object of the present invention is to provide a medical operating method which provides real time imaging in a cost effective manner.

A particular object of the present invention is to provide electronic, three-dimensional (3D) volumetric data acquisition using an ultrasonic imaging device or system. Another object of the present invention is to provide both conventional two-dimensional (2D) image and 3D image processing.

These and other objects of the present invention will be apparent from the drawings and descriptions herein.

SUMMARY OF THE INVENTION

A medical system comprises, in accordance with the present invention, a carrier and a multiplicity of electromechanical transducers mounted to the carrier, the transducers being disposable in effective pressure-wave-transmitting contact with a patient. Energization componentry is operatively connected to a first plurality of the transducers for supplying the same with electrical signals of at least one pre-established ultrasonic frequency to produce first pressure waves in the patient. A control unit is operatively connected to the energization componentry and includes an electronic analyzer operatively connected to a second plurality of the transducers for performing electronic 3D volumetric data acquisition and imaging (which includes determining three-dimensional shapes) of internal tissue structures of the patient by analyzing signals generated by the second plurality of the transducers in response to second pressure waves produced at the internal tissue structures in response to the first pressure waves. The control unit includes phased-array signal processing circuitry for effectuating an electronic scanning of the internal tissue structures which facilitates one-dimensional (vector), 2D (planar) and 3D (volume) data acquisition. Vector data acquisition is a special case of planar data acquisition, which is a special case of volume data acquisition.

In a specific embodiment of the invention, the carrier is rigid. More specifically, the carrier comprises a plurality of rigid modular substrates rigidly connected to one another, each of the substrates holding a plurality of the transducers. The modular substrates are off-the-shelf components such as the 1.5D (or 1.75D) transducer arrays found in conventional, premium probes, with on the order of 100 piezoelectric transducers (or elements) disposed in a tightly packed line along a length dimension of the substrate. Inter-element spacing is typically one wavelength or less to support full scanning along the length dimension. A width dimension of a modular substrate carries substantially fewer (e.g. less than 10) piezoelectric transducers. Both the inter-element spacing and element size along the width dimension is typically a few or several wavelengths. The electronic scanning of internal tissue structures of a patient along the length dimension is performed conventionally by the control unit. The control unit also provides electronic scanning of internal tissue structures of a patient in the width dimensions of the modular substrates, where the density of the transducers is low, using a procedure unique to the present invention which is described in detail below. The rigid carrier may be planar (flat) or curved in its shape so as to be conformal to a patient's body.

The carrier may be provided with a fluid-filled flexible bag disposable in contact with the patient for facilitating transmission of the first pressure waves into the patient from the first plurality of transducers and reception of the second pressure waves by the second plurality of transducers.

In accordance with a feature of the present invention, the phased-array signal processing circuitry includes switching circuitry or other means operatively connected to the energization componentry for independently varying the time-delays or phases of the electrical signals across the first plurality of the transducers to effectuate an electronic scanning of the internal tissue structures of the patient by the first pressure waves. Alternatively or additionally, the phased-array signal processing circuitry includes switching circuitry or other means for varying sampling times or phases of the second pressure waves received at the second plurality of the transducers and further includes combining circuitry for combining the sampled signals to effectuate an electronic scanning of the second pressure waves by the second plurality of transducers. The effect of the aforementioned phased-array signal processing circuitry is to dynamically focus the pressure waves into spatially directed beams of energy and to provide electronic sequential beam scanning and/or beam steering in order to interrogate the internal tissue structures of the patient. The principles of sequential beam scanning and beam steering are known to those skilled in the art.

The transmitting transducers may be used also for receiving. However, there may be transducers which are dedicated to one task or the other.

In accordance with another feature of the present invention, the control unit includes circuitry operatively connected to the energization componentry for varying the frequency to facilitate collection of three-dimensional structural data pertaining to tissue structures at different depths in the patient.

A system in accordance with the present invention is generally useful in the generation of 2D and 3D images of internal tissue structures of a living being such as a human medical patient. To that end, at least one display is operatively connected to the electronic analyzer for providing an image of the internal tissue structures of the patient.

A related medical method comprises, in accordance with the present invention, (a) placing a carrier holding a multiplicity of electromechanical transducers and a patient adjacent to one another so that the transducers are disposed in effective pressure-wave-transmitting contact with the patient, (b) supplying a first plurality of the transducers with electrical signals of at least one pre-established ultrasonic frequency to produce first pressure waves in the patient, (c) receiving, via a second plurality of the transducers, second pressure waves produced at internal tissue structures of the patient in response to the first pressure waves, and (d) performing electronic 3D volumetric data acquisition by solely an electronic scanning of said internal tissue structures and performing electronic 3D imaging (which includes determining three-dimensional shapes) of the internal tissue structures in part by analyzing signals generated by the second plurality of the transducers in response to the second pressure waves. At least one of the supplying and receiving steps is executed to effectuate electronic scanning of the internal tissue structures.

The electronic scanning may be accomplished by varying the time delays or phases of the electrical signals across the first plurality of the transducers to effectuate a phased-array electronic scanning of internal tissues of the patient by the first pressure waves. Alternatively or additionally, the electronic scanning is accomplished by varying sampling times or phases of the second plurality of the transducers to effectuate an electronic scanning of the second pressure waves by the second plurality of transducers. In the former case, the varying of the time delay or phase of the electrical signals may include operating switching circuitry operatively connected to the first plurality of the transducers. In the latter case, the varying of the time delay or phase of the electrical signals may include operating switching circuitry operatively connected to the second plurality of the transducers.

The method preferably further comprises disposing a flexible fluid-filled bag between the patient and the carrier and transmitting the first pressure waves and receiving the second pressure waves through the fluid filled flexible bag. The flexible bag ensures positive pressure wave transmission and reception and effectively conforms the ultrasonic system to the irregular body profile of the patient.

A medical system comprises, in accordance with another conceptualization of the present invention, a carrier, a multiplicity of electromechanical transducers mounted to the carrier, and energization componentry operatively connected to a first plurality of the transducers for supplying the same with electrical signals of at least one pre-established ultrasonic frequency to produce first pressure waves in the patient. The system further comprises a control unit operatively connected to the energization componentry for operating the same to produce the first pressure waves in the patient. The control unit includes an electronic analyzer operatively connected to a second plurality of the transducers for performing electronic 3D volumetric data acquisition and imaging of internal tissues of the patient by analyzing signals generated by the second plurality of the transducers in response to second pressure waves produced at internal tissues of the patient in response to the first pressure waves. The control unit is operatively connected to the second plurality of the transducers to gather and organize data from the second plurality of the transducers so that the second plurality of transducers define a plurality of data gathering apertures which are unique to this invention. A subset of the second plurality of the transducers is used in each data gathering aperture. Data can be gathered from the defined data gathering apertures sequentially in time or simultaneously. Electronic scanning is performed by each data gathering aperture to interrogate and acquire structural data from a desired spatial region. The control unit includes coherent aperture combining (CAC) circuitry for coherently combining structural data from the respective data gathering apertures, which is a unique feature of this invention. The resultant effective increase in total aperture size improves the resolution capability of the imaging system. The control unit may also include circuitry for noncoherently combining structural data, which allows extended images to be created without increasing the imaging resolution.

In a particular embodiment of the present invention, the transducers are disposed on or form rigid substrates in turn movably connected to one another, e.g., via a flexible web carrier. In this embodiment, the individual substrates form separate data gathering apertures, and the coherent aperture combining circuitry includes or is connected to position determination elements for determining relative positions and orientations of the substrates relative to one another. The position determination elements may include a multiplicity of point scatterers, a subset of which are visible to (i.e., can be scanned by) each of the substrates in question, the position determination element further including programmed componentry operatively connected to the energization componentry for periodically scanning the point scatterers with first ultrasonic pressure waves and calculating instantaneous positions of the point scatterers as seen by each substrate in question using the reflected second ultrasonic pressure waves. Alternatively, the first ultrasonic pressure wave signals received directly by a plurality of distinct transducers (different from those used to generate the first pressure waves) can be used in place of point scatterers (and their associated reflected second pressure waves) to calculate the instantaneous positions of the distinct transducers as seen by each of the substrates in question. In either case, the position determination elements include circuitry for executing computations according to a self-cohering algorithm that computes each substrate's relative position and orientation using the instantaneous position measurements, and adjusts the signals from the coherently combined apertures so they can be added together constructively.

For medical diagnostic and treatment purposes, at least one display is operatively connected to the electronic analyzer for providing an image of the internal tissue structures of the patient.

An associated medical method comprises, in accordance with the present invention, (i) providing a carrier holding a multiplicity of electromechanical transducers forming a plurality of data gathering apertures, (ii) placing the carrier and a patient adjacent to one another so that the transducers are disposed in effective pressure-wave-transmitting contact with the patient, (iii) supplying a first plurality of the transducers with electrical signals of at least one pre-established ultrasonic frequency to produce first pressure waves in the patient, (iv) receiving, via a second plurality of the transducers, second pressure waves produced at internal tissue structures of the patient in response to the first pressure waves, and (v) performing electronic 3D volumetric data acquisition and imaging (which includes determining three-dimensional shapes) of the internal tissue structures by analyzing signals generated by the second plurality of the transducers in response to the second pressure waves.

The carrier may take any of several forms. In one form, the carrier is a flexible web, with the transducers being individual scalar elements distributed in an array throughout at least a substantial portion of the web. In this case, the various data gathering apertures are defined by signal processing: either the first plurality of transducers is energized in groups, or the second plurality of transducers is sampled (i.e. received) in groups, or both. This electronic grouping of transducers may be varied from instant to instant, depending on the imaging requirements. In another form of the carrier, a plurality of rigid carrier substrates are movably attached to one another (e.g., via a flexible web or sheet), each substrate bearing a respective set of scalar transducer elements. The substrates with their respective transducers easily or conveniently (but not necessarily) define respective data gathering apertures. In either of these forms of the carrier, one or both of the steps of transmitting and receiving may include coherently combining structural data from the respective apertures using CAC. In both cases, a self-cohering algorithm is used to compute relative positions and orientations of the transducer scalar elements or rigid carrier substrates, as the case may be, using instantaneous position measurements and to adjust signals from each coherently combined aperture to enable constructive addition of those signals from the coherently combined apertures.

The carrier may alternatively take the form of a singular rigid structure constructed using scalar transducer elements arranged in the likeness of an array, or a rigid form constructed from a plurality of modular rigid substrates (where each substrate consists of one or more 1D or 1.5D arrays, and where each array contains a plurality of scalar transducer elements) rigidly connected to one another and arranged in the likeness of an array. In these cases, the positions and orientations of all transducers relative to each other are known; no calibration or position determination circuitry is necessary. Signal transmission apertures and data gathering apertures are formed and used to electronically scan desired regions and electronically acquire 3D volumetric data. Each signal transmission aperture is formed by grouping a first plurality of transducer elements and each data gathering aperture is formed by grouping a second plurality of transducer elements. Coherent aperture combining can be used to combine the structural data from multiple data gathering apertures without a self-cohering algorithm. Noncoherent combination of structural data from respective apertures may also be performed.

Where CAC is employed to combine structural data from multiple data gathering apertures and the relative positions and orientations of those apertures are unknown, the coherent combining of structural data preferentially includes determining relative positions and orientations of the data gathering apertures relative to one another. Where point scatterers are visible to transducers on the data gathering apertures, the determining of relative positions and orientations of these apertures includes periodically scanning, using a plurality of transducer elements on the respective apertures, of the point scatterers with first ultrasonic pressure waves and calculating the instantaneous positions of the point scatterers as seen by the respective plurality of transducer elements using reflected pressure waves. Where a distinct plurality of transducers are used in place of point scatterers, direct measurements of pressure waves received by those distinct transducers are used to calculate the instantaneous positions of those distinct transducers relative to respective plurality of transducers transmitting the first pressure waves. In either case, the determining of relative positions and orientations of the data gathering apertures entails executing computations according to a self-cohering algorithm.

BRIEF DESCRIPTION OF THE DRAWINGS

FIG. 11 is a block diagram showing a modification of the apparatus illustrated in FIG. 10.

FIG. 14 is a schematic perspective view of yet another ultrasonographic imaging device which includes a sensor vest in a closed, use configuration.

FIG. 15 is a schematic perspective view of the sensor vest of FIG. 14, showing the vest in an open configuration.

FIG. 24 is a schematic perspective view of an ultrasonographic device.

FIG. 25 is a schematic perspective view of another ultrasonographic device.

FIG. 26 is a schematic perspective view of the ultrasonographic device of FIG. 25, showing the device in use on a patient.

FIG. 29 is partially a schematic perspective view and partially a block diagram of an ultrasonic imaging system in accordance with the present invention.

FIG. 30 is a schematic perspective view, on a larger scale, of a modular transducer package or array aperture included in the system of FIG. 29.

DESCRIPTION OF THE PREFERRED EMBODIMENTS

The present invention is directed chiefly to an imaging device and particularly to an ultrasonographic imaging device utilizable in diagnostic and therapeutic procedures. The ultrasonographic imaging device of the present invention is described generally hereinafter with reference to FIG. 8 et seq. The ultrasonographic imaging device, and particularly image derivation or construction portions thereof, can be employed as an image generating apparatus or scanner 42 in the medical diagnostic system of FIG. 1 or a diagnostic image generating apparatus 78a, 78b, 78i in the medical diagnostic system of FIG. 4. Alternatively or additionally, the ultrasonographic imaging device can be employed in carrying out certain minimally invasive diagnostic or therapeutic operations, examples of which are illustrated schematically in FIGS. 12 and 13.

Figure 1:
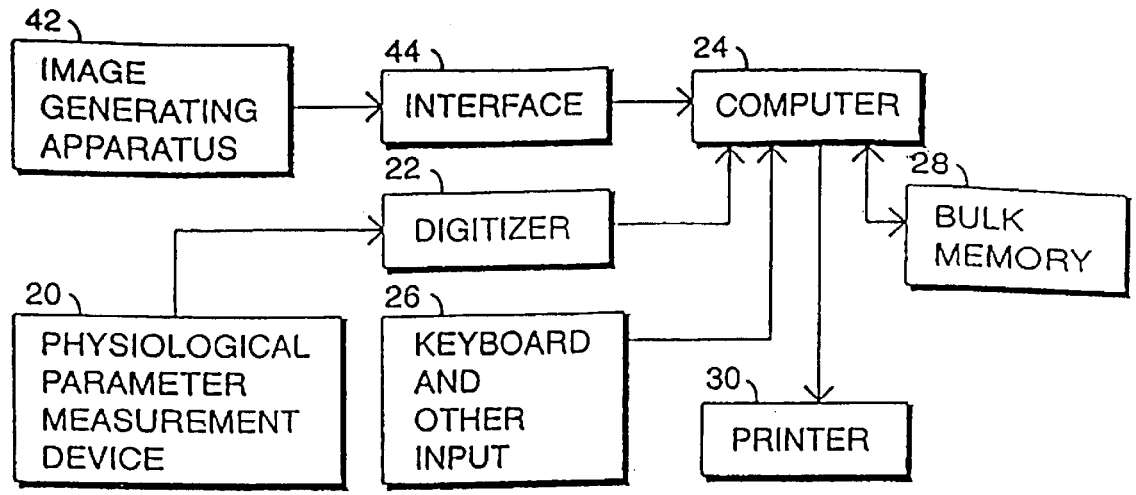
FIG. 1 is a block diagram of a medical diagnostic system, which may utilize or incorporate an ultrasonographic imaging device in accordance with the present invention.

As illustrated in FIG. 1, a medical diagnostic system comprises a device 20 for monitoring and measuring a biological or physiological parameter. Monitoring and measuring device 20 is juxtaposable to a patient for collecting individualized medical data about the patient's condition. Device 20 may take the form of an electronic thermometer, an electronic blood pressure gauge, a pulmonary function apparatus, a Doppler study apparatus, an EEG machine, an EKG machine, an EMG machine, or a pressure measurement device, etc., or include a plurality of such components.

Monitoring and measuring device 20 is connected at an output to a digitizer 22 which converts normally analog type signals into coded binary pulses and transmits the resulting digital measurement signal to a computer 24. Digitizer 22 may be incorporated into a housing (not shown) enclosing all or part of the monitoring and measuring device 20. Moreover, digitizer may be an integral part of monitoring and measuring device 20.

Computer 24 receives instructions and additional input from a keyboard 26. Keyboard 26 is used to feed computer 24 information for identifying the patient, for example, the patient's age, sex, weight, and known medical history and conditions. Such medical conditions may include past diseases and genetic predispositions.

Computer 24 is also connected to an external memory 28 and an output device 30 such as a printer or monitor. Memory 28 stores medical data for a multiplicity of previously diagnosed medical conditions which are detectable by analysis of data provided by monitoring and measuring device 20.

Figure 2:
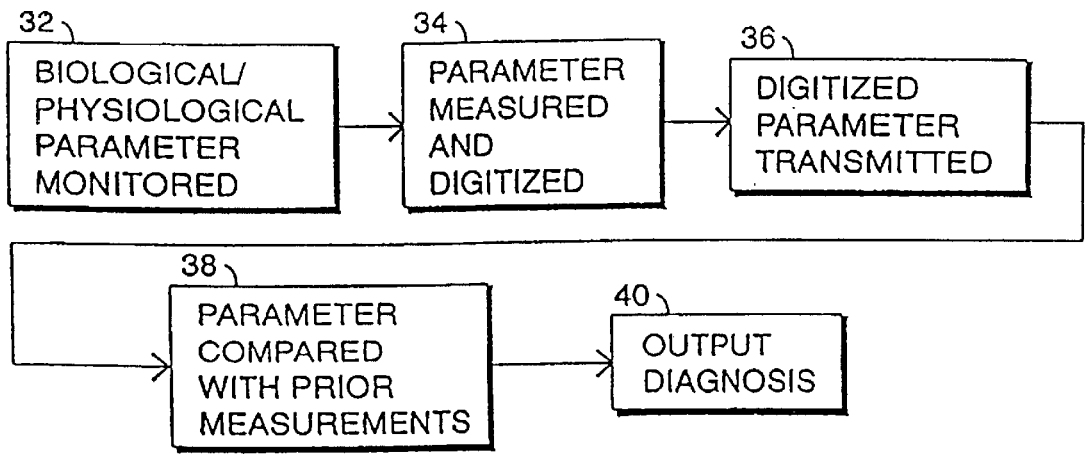
FIG. 2 is a flow-chart diagram illustrating steps in a mode of operation of the diagnostic system of FIG. 1.

As illustrated in FIG. 2, monitoring and measuring device 20 detects a magnitude of a predetermined biological or physiological parameter in a step 32. Digitizer 22 converts the detected magnitude into a pre-established digital format in a step 34 and transmits the digital signal to computer 24 in a step 36. Computer 24 is operated in a step 38 to compare the digitized data from monitoring and measuring device 20 with the data stored in memory 28 and to derive a diagnosis as to the patient's condition. The diagnosis is then communicated to the user (operator) and to the patient via output device 30 in a step 40.

If monitoring and measuring device 20 measures a physiological function characterized by a plurality of different variables, for example, the electric potential at different points on the patient's body (EEG, EKG, EMG), these variables may be broken down by computer 24 into one or more parameters, e.g., a frequency packet. The measured values of the pre-established parameters are then compared with parameter ranges stored in memory 28 for the type of parameter and the kind of patient, as characterized by sex, age, weight, etc. If the measured values of the pre-established parameters fall within expected ranges, as stored in memory 28, then computer 28 communicates a "normalcy" finding via printer 30. If, on the contrary, the measured values of one or more parameters fall outside the normal ranges, then a diagnosis of a possible medical condition is printed out.

As further illustrated in FIG. 1, the medical diagnostic system may comprise, in addition to or alternatively to monitoring and measuring device 20, image generating apparatus or scanner 42 for generating in electrically encoded form a visually readable image of an organic part of the patient. Scanner 42 may take the form of an MRI apparatus, a CAT scanner, an X-ray machine, an ultrasonography apparatus (see FIGS. 8-15 and 20), or a video camera with or without magnification optics for magnifying a sample on a slide. The video camera can be used for obtaining an image of a portion of a patient's skin.

Scanner 42 is connected via an interface 44 to computer 24.

Figure 3:
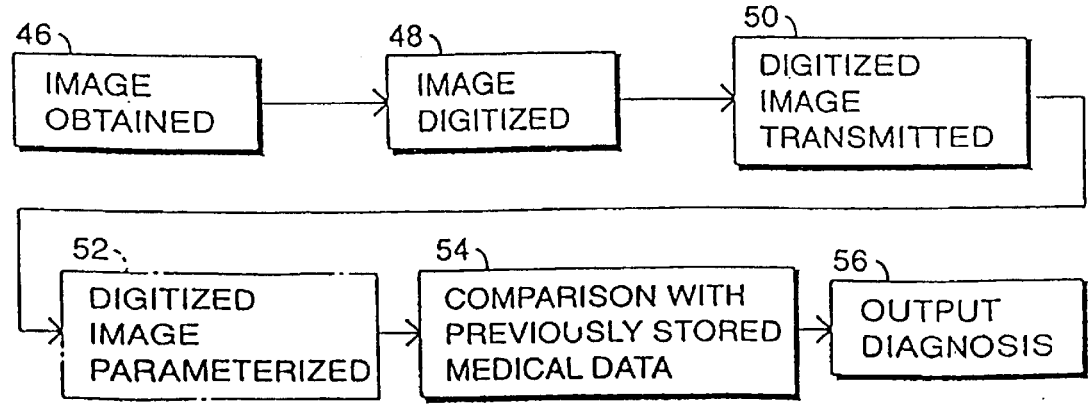
FIG. 3 is a flow-chart diagram illustrating steps in another mode of operation of the diagnostic system of FIG. 1.

As shown in FIG. 3, scanner 42 obtains an image of a tissue or organ in a step 46. The image is digitized, either by scanner 42 or interface 44 in a step 48, and is transmitted to computer 24 in a step 50. Computer 24 is operated in a step 52 to analyze the image from scanner 42 and determine specific values for a multiplicity of predetermined parameters. For example, in the event that scanner 42 takes the particular form of a video camera for dermatological diagnosis, an image of a skin surface of a patient is analyzed by computer 24 to derive such parameters as percentage of skin covered by abnormal condition, the range of sizes of individual ulcers, the range of color variation (e.g., whether bleeding is symptomatic).

The specific values of pre-established parameters calculated by computer 24 from electrically encoded images transmitted from scanner 42 are compared by computer 24 with previously determined parameter ranges stored in memory 28. For example, if a pregnant woman's fetus is being scanned by ultrasonography, the lengths of the fetal appendages, arms, legs, fingers, etc., are compared with each other and with respective fetal appendage ranges recorded in memory 28 for the stage of pregnancy, weight of the fetus, and possibly weight of the mother. In the event that any appendages are missing or are of abnormal length, a diagnosis as to possible deformity is printed out. Organs internal to the fetus may be similarly examined automatically by scanner 42 and computer 24. In more advanced stages of pregnancy, physiological functions such as the heart rate of the fetus may be automatically monitored for abnormal conditions.

The analysis performed by computer 24 on the image from scanner 42 will depend in part on the region of the patient's body being scanned. If a woman's breast or a person's cortex is being monitored for tumorous growths, computer 24 is programmed to separate the tissue image into regions of different textures. The different textured regions are parameterized as to size, shape and location and the derived parameters are compared to values in memory 30 to determine the presence of a tumor. Additional analysis is undertaken to detect lines in an image which may indicate the presence of an organic body.

A similar analysis is undertaken to evaluate a tissue specimen on a slide. The texture and line scanning may be repeated at different magnification levels if, for example, the tissue sample is a slice of an organ wall. On a high magnification level, the texture and line analysis can serve to detect microorganisms in blood.

Memory 28 may store entire images related to different diseases. For example, memory may store images of skin conditions in the event that scanner 42 takes the form of a video camera at a dermatological diagnosis and treatment facility. In a step 54 (FIG. 3), computer 24 compares the image of a patient's skin with previously stored images in memory 28, for example, by breaking down the current image into sections and overlaying the sections with sections of the stored images, at variable magnification levels.

In the event that scanner 42 takes the form of an MRI apparatus, a CAT scanner or an ultrasonographic scanner such as those described hereinafter with references to FIGS. 8-15 and 20, the images stored in memory 28 are of internal organic structures. In step 54 (FIG. 3), computer 24 compares images of a person's internal organs with previously stored organ images in memory 28. Computer 24 partitions the image from the MRI apparatus or CAT scanner into subareas and overlays the subareas with sections of the stored images, at variable magnification levels.

In a final step 40 (FIG. 3), computer 24 communicates the results of its diagnostic evaluation to a user or patient.

Figure 4:
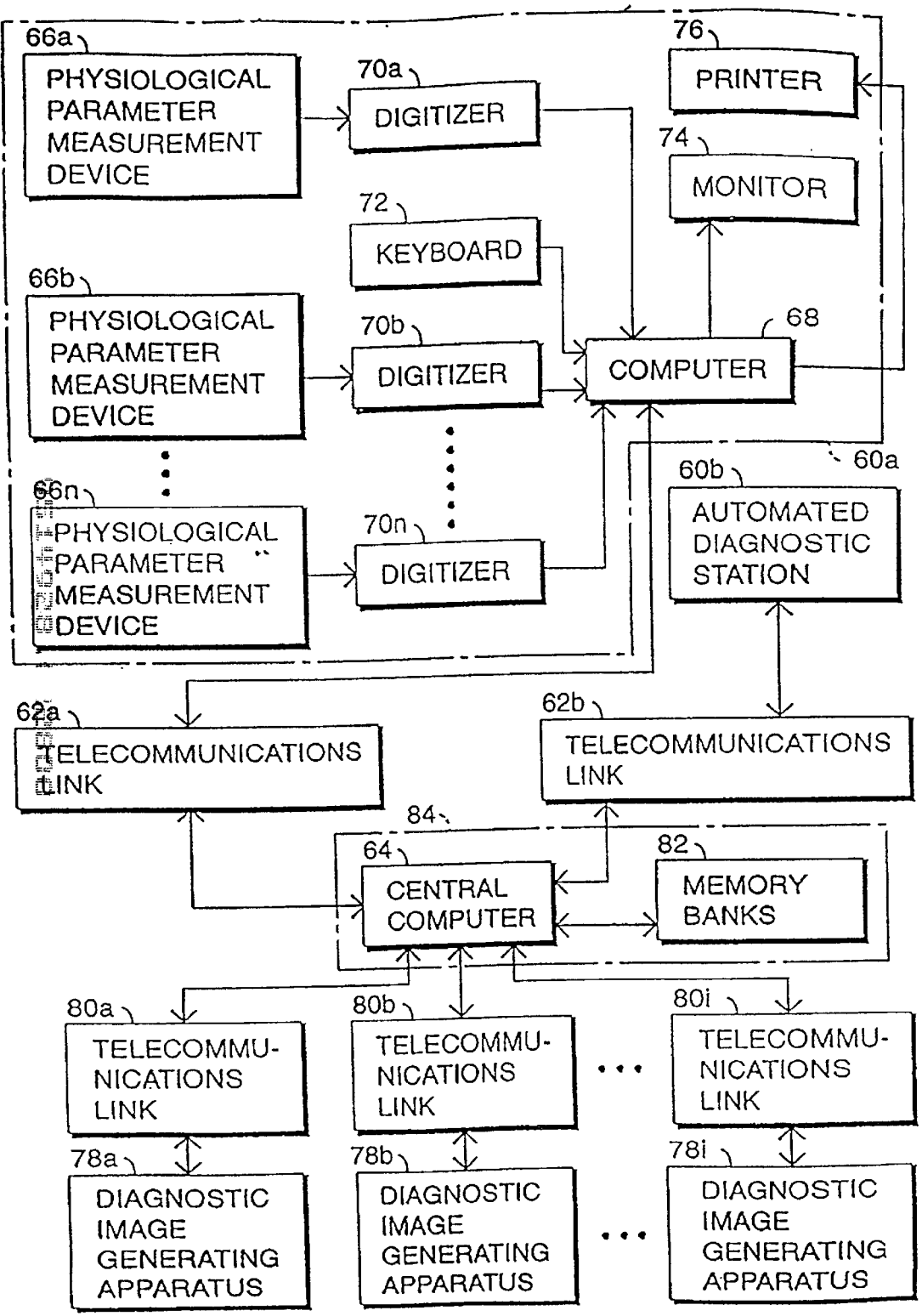
FIG. 4 a block diagram of a further medical diagnostic system.

As illustrated in FIG. 4, a medical diagnostic system comprises a plurality of remote automated diagnostic stations 60a and 60b connected via respective telecommunications inks 62a and 62b to a central computer 64. Each diagnostic station 60a, 60b may take the form shown in FIG. 1, local computer 24 communicating via link 62a, 62b with central computer 64. Alternatively, each diagnostic station 60a, 60b may take the form shown in FIG. 4 and include a respective plurality of monitoring and measuring devices 66a, 66b, . . . 66n operatively connected to a local computer 68 via respective digitizer output units 70a, 70b, . . . 70n. Computer 68 is fed instructions and data from a keyboard 72 and communicates diagnostic results via a monitor 74 or printer 76. As discussed hereinabove with reference to monitoring and measuring device 20 of FIG. 1, each monitoring and measuring device 66a, 66b, ... 66n is juxtaposable to a patient for collecting individualized medical data about the patient's condition. Monitoring and measuring devices 66a, 66b, ... 66n may respectively take the form of an electronic thermometer, an electronic blood pressure gauge, a pulmonary function apparatus, a Doppler study apparatus, an EEG machine, an EKG machine, an EMG machine, or a pressure measurement device, etc.

Digitizers 70a, 70b, ... 70n convert normally analog type signals into coded binary pulses and transmit the resulting digital measurement signals to computer 68. Digitizers 70a, 70b, ... 70n may be incorporated into the housings or casing (not shown) enclosing all or part of the respective monitoring and measuring devices 66a, 66b, ... 66n.

Keyboard 72 is used to feed computer 68 information for identifying the patient, for example, the patient's age, sex, weight, and known medical history and conditions. Such medical conditions may include past diseases and genetic predispositions.

As further illustrated in FIG. 4, a plurality of diagnostic image generating apparatuses or scanners 78a, 78b, ... 78i are also connected to central computer 64 via respective hard-wired or wireless telecommunications links 80a, 80b, ... 80i. Scanners 78a, 78b, ... 78i each generate in electrically encoded form a visually readable image of an organic part of the patient. Scanners 78a, 78b, ... 78i may each take the form of an MRI apparatus, a CAT scanner, an X-ray machine, an ultrasonography apparatus (FIGS. 8-15 and 20), or a video camera with or without magnification optics for magnifying a sample on a slide.

Because of the enormous quantity of data necessary for storing images, central computer 64 is connected to a bank of memories 82 at a central storage and information processing facility 84. Diagnosis of patient conditions may be undertaken by central computer 64 alone or in cooperation with local computers 24 or 68.

Figure 5:
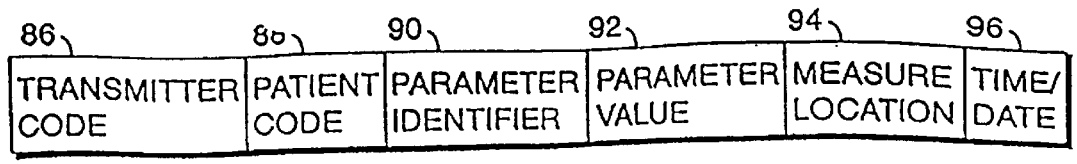
FIG. 5 is a diagram showing the composition of a data string or module used in the system of FIG. 4.

As illustrated in FIG. 5, local computers 24 and 68 transmit information to central computer 64 in data packets or modules each include a first string of binary bits 86 representing the transmitting station 60a, 60b, a second bit string 88 identifying the patient, a bit group 90 designating the parameter which is being transmitted, another bit group 92 coding the particular measured value of the parameter, a set of bits 94 identifying the point on the patient at which the measurement was taken, and another bit set 96 carrying the time and date of the measurement. Other bit codes may be added as needed.

Figure 6:
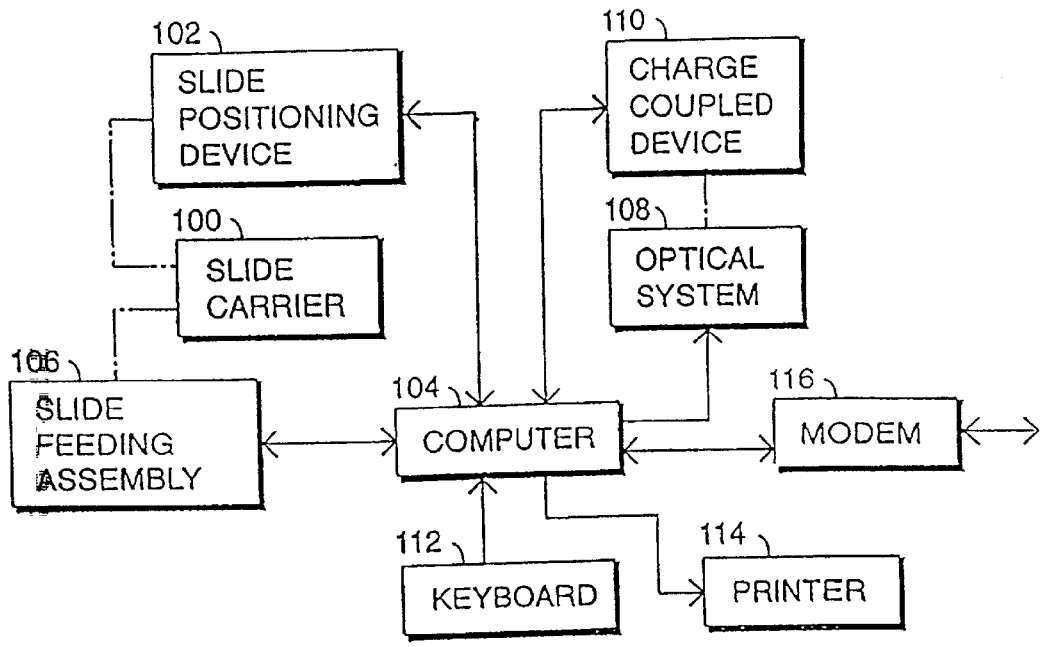
FIG. 6 is a block diagram of a computerized slide scanning system.

As shown in FIG. 6, a computerized slide scanning system comprises a slide carrier 100 mountable to a microscope stage and a slide positioning device 102 mechanically linked to the slide carrier 100 for shifting the carrier along a path determined by a computer 104. Computer 104 may be connected to an optional transport or feed assembly 106 which delivers a series of slides (not shown) successively to slide carrier 100 and removes the slides after scanning.

Computer 104 is also connected to an optical system 108 for modifying the magnification power thereof between successive slide scanning phases. Light emerging from optical system 108 is focused thereby onto a charge coupled device ("CCD") 110 connected to computer 104 for feeding digitized video images thereto.

Computer 104 performs a line and texture analysis on the digitized image information from CCD 110 to determine the presence of different organic structures and microorganisms. The different textured regions are parameterized as to size, shape and location and the derived parameters are compared to values in a memory to identify microscopic structures. The texture and line scanning is repeated at different magnification levels.

Computer 104 may be connected to a keyboard 112, a printer 114, and a modem 16. Modem 116 forms part of a telecommunications link for connecting computer 104 to a remote data processing unit such as computer 64 in FIG. 4.

Image generating apparatus 42 in FIG. 1 may take the form of the computerized slide scanning system of FIG. 6.

Figure 7:
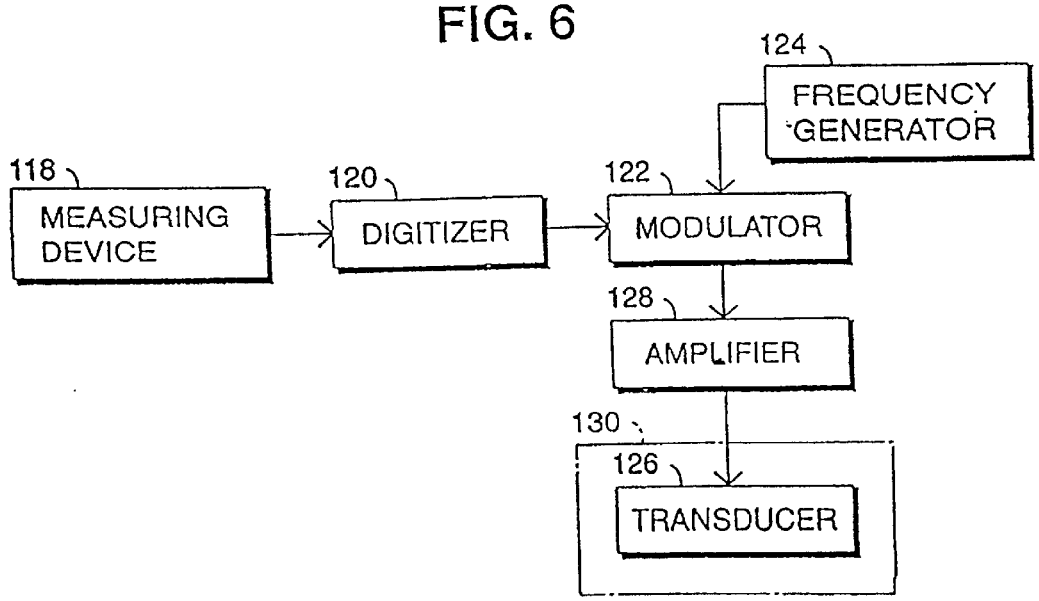
FIG. 7 is a block diagram of a device for measuring a diagnostic parameter and transmitting the measurement over the telephone lines.

As shown in FIG. 7, a device for measuring a diagnostic parameter and transmitting the measurement over the telephone lines comprises a monitoring and measuring device 118 which may take the form, for example, of an electronic thermometer, an electronic blood pressure gauge, a pulmonary function apparatus, a Doppler study apparatus, an EEG machine, an EKG machine, an EMG machine, or a pressure measurement device, etc., or include a plurality of such components. Monitoring and measuring device 118 is connected at an output to a digitizer 120 which in turn is coupled to a modulator 122. Modulator 122 modulates a carrier frequency from a frequency generator 124 with the data arriving from monitoring and measuring device 118 via digitizer 120 and transmits the modulated signal to an electroacoustic transducer 126 via an amplifier 128. Transducer 126 is removably attachable via a mounting element 130 to the mouthpiece of a telephone handset (not shown) and generates a pressure wave signal which is converted by a microphone in the handset mouthpiece back to an electrical signal for transmission over the telephone lines. Of course, transducer 126 may be omitted and modulator 122 connected directly to a telephone line.

The system of FIG. 7 enables the transmission of specialized medical data directly over the telephone lines to a central computer (e.g. computer 64 in FIG. 4) which utilizes the incoming data to perform a diagnostic evaluation on the patient.

Monitoring and measuring device 118 may include traditional medical instrumentation such as a stethoscope or modern devices such as a CCD.

Figure 8:
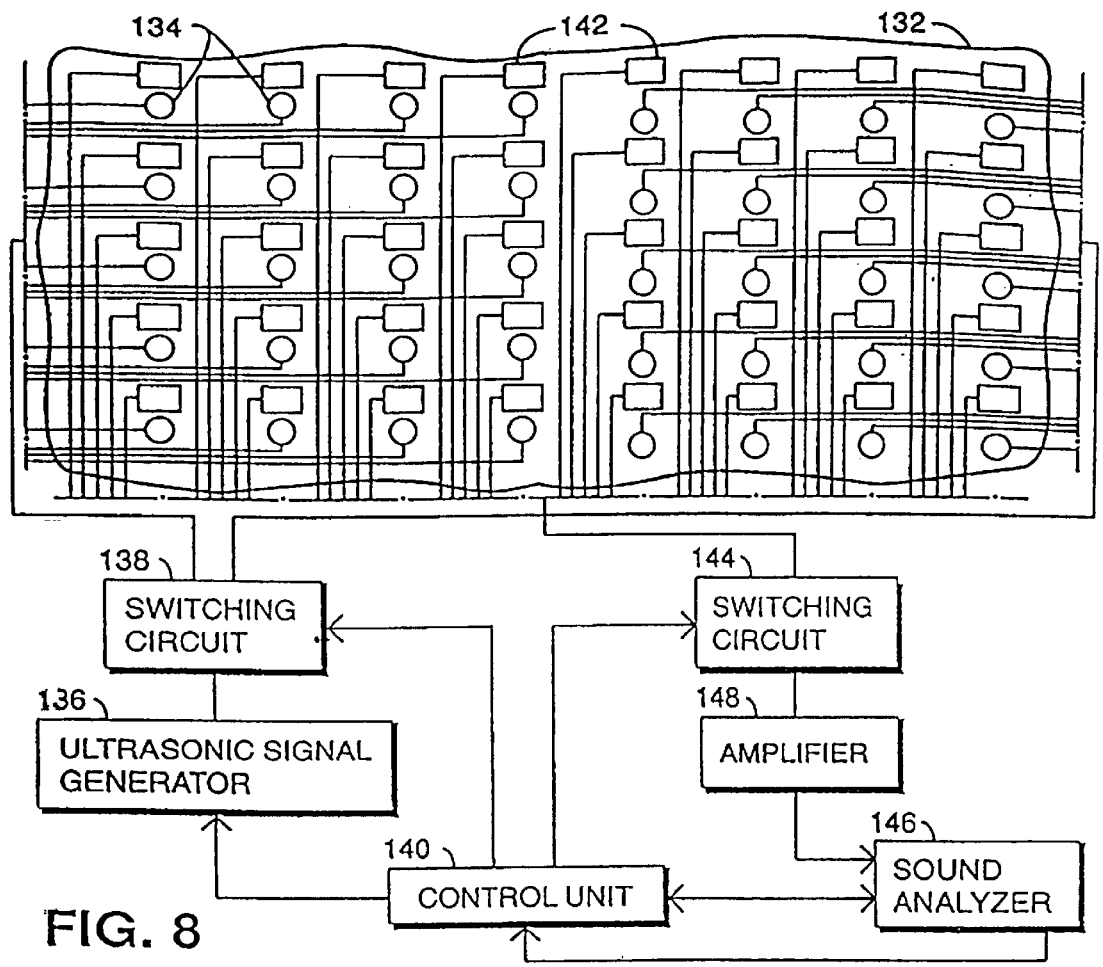
FIG. 8 is a diagram of an ultrasonography device.

FIG. 8 shows an ultrasonographic image generating apparatus which may be used in the medical diagnostic system of FIG. 1 (see reference designation 42) or in the medical diagnostic system of FIG. 4 (see reference designations 78a, 78b, ... 78i). As will be apparent from the following descriptions, the ultrasonographic image generating apparatus utilizes ultrasonic pressure waves to obtain three-dimensional structural information pertaining to a patient's internal tissues and organs. As shown in FIG. 8, a flexible web 132 carries a plurality of electromechanical transducers 134 particularly in the form of piezoelectric electroacoustic crystal elements disposed in a substantially rectangular array. Transducers 134 are each connectable to an ultrasonic signal generator 136 via a switching circuit or multiplexer 138. Switching circuit 138 is operated by a control unit 140 to connect transducers 134 to signal generator 136 in a predetermined sequence, depending on the area of a patient's body which is being ultrasonically scanned. The sequence in which transducers 134 are connected to signal generator 136 may include phase shifts or time delays to implement an electronic scan of the patient's internal tissues, as discussed below with reference, for example, to FIG. 32.

Web 132 also carries a multiplicity of electromechanical, specifically acoustoelectric, transducers particularly in the form of transducers or sensors 142 also arranged in a substantially rectangular array. Sensors 142 are connected to a switching circuit 144 also operated by control unit 140. An output of switching circuit 144 is connected to a sound or pressure wave analyzer 146 via an amplifier 148.

The sequence in which sensors 142 are connected to pressure wave analyzer 146 may be such as to enable or facilitate an organization of sensor responses into predetermined groupings defining respective data gathering apertures. The grouping of sensors 142 may be an instantaneous grouping, varied instant by instant pursuant to real-time imaging requirements. Generally, the larger the apertures (the larger the areas of the respective groupings), the higher the resolution of the three-dimensional ("3D") volumetric data acquisition and of the imaging of the ultrasonographic system. Where the outputs of sensors 142 are sampled or interrogated in groups so as to form a plurality of data gathering apertures, control unit 140 includes coherent aperture combining circuitry (See FIG. 29) for coherently combining structural data from the respective apertures. In this case, position determination circuitry in control unit 140 and/or sound analyzer 146 executes computations according to a self-cohering algorithm that computes the relative positions and orientations of the data gathering apertures using instantaneous position measurements and adjusts the signals from the coherently combined apertures so they can be added together constructively. The resultant effective increase in total aperture size improves the resolution capability of the imaging system. Electronic scanning performed by each data gathering aperture also requires position determination circuitry that computes the relative positions of the sensors 142 themselves (since they are contained in a flexible web). Control unit 140 may also include the option of noncoherently combining structural data, which allows extended images to be created without increasing the imaging resolution.

The sequence in which sensors 142 are connected to analyzer 146 by switching circuit or multiplexer 144 may include phase shifts or time delays to implement an electronic scan of the patient's internal tissues, as discussed below.

Electroacoustic transducers 134 and sensors 142 may be implemented in the form of packaged modular arrays of piezoelectric crystals, as discussed hereinafter with reference to FIG. 29. At the present time, such packages are generally linear arrays of some one hundred or more piezoelectric crystal elements. Some modified linear arrays contain several linear arrays so that a transverse or width dimension has up to ten crystal elements.

FIG. 8 shows electroacoustic transducers 134 and sensors 142 as being separate, so that they perform dedicated generating (i.e., transmitting) and receiving functions, respectively. It is also possible, however, to provide a multiplicity of piezoelectric electromechanical transducers or arrays of transducer elements which perform both the transmitting and the receiving functions. Various combinations of functions are also possible. For example, some transducer arrays may function as both transmitters and receivers, while other transducer arrays function only as receivers. The various operating potentialities are discussed in greater detail below with reference to FIG. 29.

Web 132 is draped over or placed around a portion of a patient's body which is to be monitored ultrasonically. Control unit 140 then energizes signal generator 136 and operates switching circuit 138 to activate transducers 134 in a predetermined sequence. Each transducer 134 may be a multiple-element aperture. In that case, several piezoelectric elements or scalar excitation transducers are energized simultaneously with the excitation waveform where appropriate phases shifts or time delays are applied to effectuate electronic scanning. Depending on the transducer or combination of transducers 134 which are activated, control unit 140 operates switching circuit 144 to connect a predetermined sequence of sensors 142 to pressure wave analyzer 146. Again, each sensor 142 may be a multiple-element aperture, whereby a plurality of piezoelectric crystals are monitored simultaneously to receive a reflected pressure waveform. Pressure wave analyzer 146 and control unit 140 cofunction to provide electronic 3D volumetric data acquisition and to determine three dimensional structural shapes from the echoes detected by sensors 142. The volumetric data acquisition is performed by solely the electronic scanning of the three dimensional structural shapes.

Control unit 140 is connected to ultrasonic signal generator 136 for varying the frequency of the generated signal. Generally, the higher the frequency, the greater the penetration into organic tissues for focusing purposes. Thus, a range of frequencies is useful for obtaining sufficient data to construct electrically or digitally encoded three-dimensional models of internal tissue and organ structures of a patient.

Figure 9:
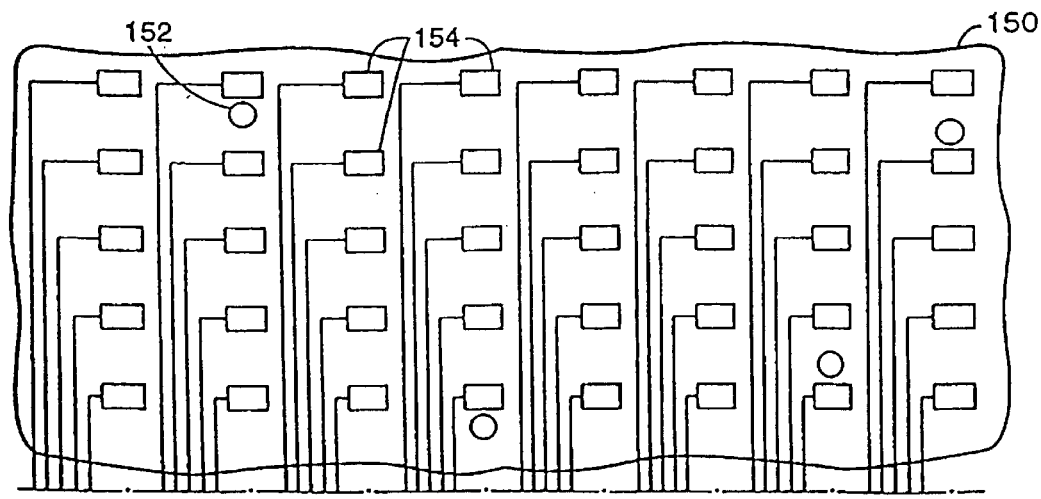
FIG. 9 is a diagram showing a modification of the device of FIG. 8.

FIG. 9 shows a modified ultrasonography web 150 having a limited number of electromechanical or electroacoustic transducers 152 and generally the same number and disposition of electromechanical or acoustoelectric sensors 154 as in web 132.

Web 132 or 150 may be substantially smaller than illustrated and may correspondingly carry reduced numbers of transducers 134 and 152 and sensors 142 and 154. Specifically, web 132 or 150, instead of being a sheet large enough to wrap around a torso or arm of a patient, may take a strip-like form which is periodically moved during use to different, predetermined locations on the patient. Control unit 140 and pressure wave analyzer 146 are programmed to detect internal organic structures from the data obtained at the different locations that the web 132 or 150 is juxtaposed to the patient.

Figure 10:
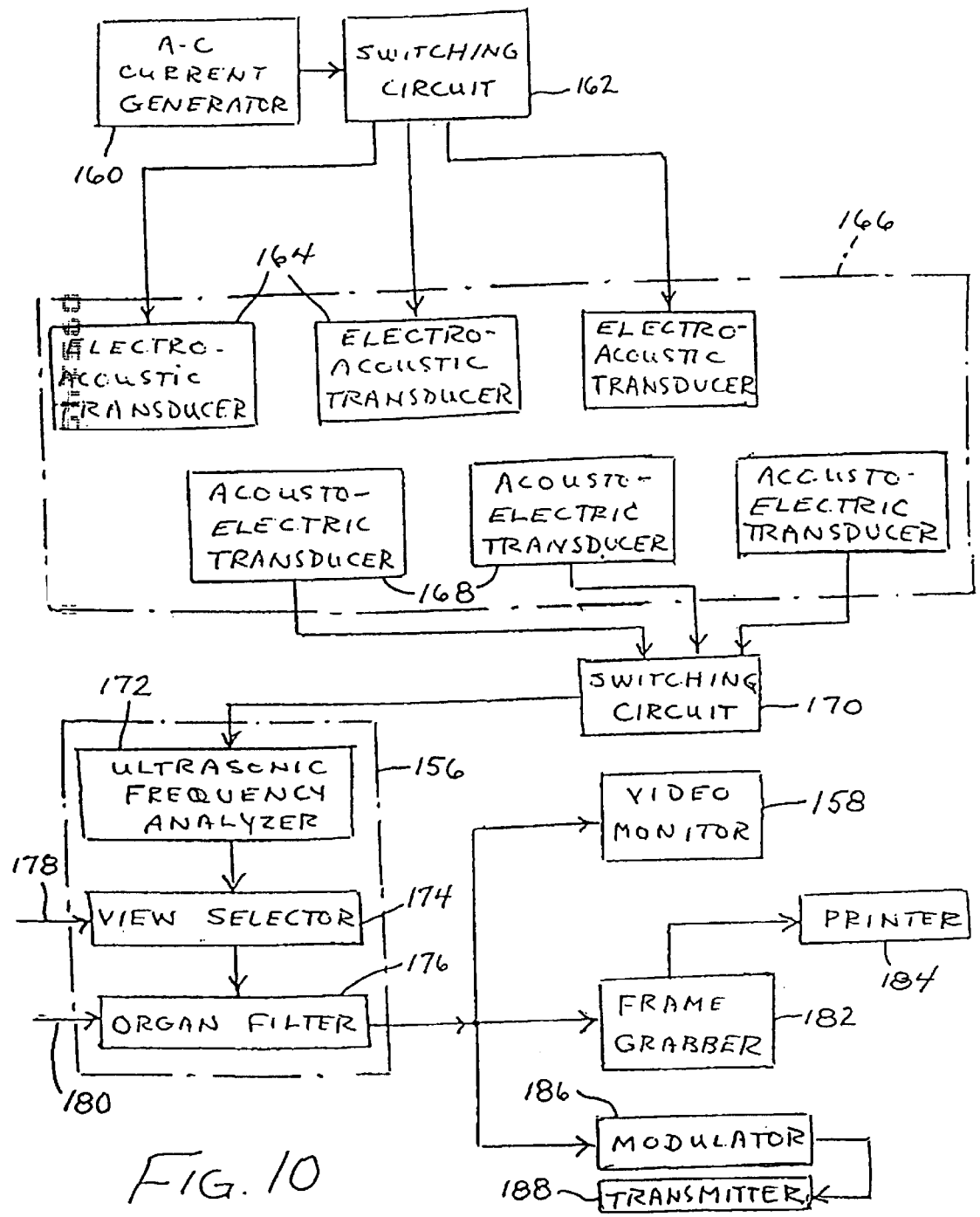
FIG. 10 is a block diagram of an ultrasonographic imaging apparatus similar to the device of FIGS. 8 and 9, for use in diagnostic and therapeutic procedures.

FIG. 10 illustrates a modification of the ultrasonography apparatus of FIGS. 8 and 9 which is employable in diagnostic or therapeutic operations involving the insertion of an instrument into a patient. A control unit 156 for performing operations of control unit 140 is connected at an output to a video monitor 158. As discussed hereinafter with reference to FIGS. 12 and 13, a diagnostician, surgeon or other medical specialist inserts a distal end of a medical instrument into a patient in response to video feedback provided by the ultrasonography apparatus including video monitor 158.

As further illustrated in FIG. 10, an a-c current or ultrasonic signal generator 160 is connected via a multiplexer or switching circuit 162 to different piezoelectric type electroacoustic transducers 164 in seriatim. Transducers 164 are mounted in interspaced fashion to a flexible web 166 which also carries an array of spaced piezoelectric type acoustoelectric transducers 168.

Web 166 is placed adjacent to a skin surface of a patient. In some cases, with any of the ultrasonic sensing devices described herein, it may be beneficial to provide a layer of fluid (e.g., water, gel) between the skin surface of the patient and the respective transducer carrier (e.g., web 166) to facilitate ultrasonic wave transmission from the electroacoustic transducers to the patient and from the patient back to the acoustoelectric transducers or sensors. In some specific embodiments of an ultrasonic imaging device discussed herein, a fluid-filled bag is used to optimize pressure wave transmission between a transducer carrier and a skin surface of a patient. Another kind of interface facilitating ultrasonic wave conduction is a moldable solid or semisolid such as wave-conductive plastic material, known in the art.

In response to the periodic energization of transducers 164, ultrasonic pressure waves are reflected from internal organic structures of the patient and sensed by acoustoelectric transducers 168. Electrical signals generated by transducers 168 in response to the reflected pressure waves are fed via a multiplexer or switching circuit 170 to control unit 156.

As discussed hereinabove with reference to control unit 140 in FIG. 8, control unit 156 controls switching circuits 162 and 170 to energize emitting transducers 164 in a predetermined sequence and to selectively couple receiving transducers 168 in a pre-established sequence to a pressure wave or ultrasonic frequency analyzer 172 in control unit 156. The sequencing depends in part on the portion of the patient being monitored.

As further discussed above with reference to FIG. 8, the sequence in which receiving transducers 168 are sampled or interrogated by switching circuit 170 may organize sensor response into predetermined groupings defining respective data gathering apertures. Control unit 156 and particularly ultrasonic frequency analyzer 172 thereof operates to coherently combine structural data from the respective apertures, with the execution of a self-cohering algorithm which computes the relative positions and orientations of receiving transducers 168 (or data gathering apertures) using instantaneous position measurements and which adjusts the signals from the coherently combined apertures so they can be added together constructively. The sequencing of transducer energization or excitation, as well as the sampling of outputs of sensors, may also be carried out to execute a phased-array-type electronic scan of internal tissues.

In addition to pressure wave or ultrasonic frequency analyzer 172, control unit 156 includes a view selector 174 and a filter stage 176. View selector 174 is operatively connected at an input to analyzer 172 and at an output to video monitor 158 for selecting an image for display from among a multiplicity of possible images of the internal organs detected by analyzer 172. View selector 174 may be provided with an input 178 from a keyboard (not shown) or other operator interface device for enabling an operator to select a desired view. For example, during the insertion of a medical diagnostic or treatment instrument into the patient or during manipulation of that instrument to effect an operation on a targeted internal organ of the patient, the medical practitioner may sequentially select views from different angles to optimize the practitioner's perception of the spatial relation between the distal tip of the instrument and the patient's internal organs.

Filter stage 176 is operatively connected to analyzer 172 and video monitor 158 for optionally eliminating a selected organ from the displayed image. Filter stage 176 is provided with an input 180 from a keyboard (not shown) or other operator interface device for enabling an operator to select an organ for deletion from the displayed image. In one example of the use of filter stage 176, blood moving through a vessel of the vascular system is deleted to enable viewing of the blood vessel walls on monitor 158. This deletion is easily effected starting from conventional techniques such as the Doppler detection of moving bodies.

Filter stage 176 may also function to highlight selected organs. The pattern recognition techniques discussed above are used to detect selected organs. The highlighting may be implemented exemplarily through color, intensity, cross-hatching, or outlines.

As further illustrated in FIG. 10, control unit 156 is optionally connected at an output to a frame grabber 182 for selecting a particular image for reproduction in a fixed hard copy via a printer 184. In addition, as discussed hereinabove with respect to the telecommunications links 80a, 80b . . . 80i in FIG. 4, ultrasonically derived real-time image information may be encoded by a modulator 186 onto a carrier wave sent to a remote location via a wireless transmitter 188.

FIG. 11 depicts the ultrasonography apparatus of FIG. 10 in a form wherein control unit 156 (FIG. 10) is realized as a specially programmed general purpose digital computer 190. A switching circuit or multiplexer 192 relays signals incoming from respective acoustoelectric transducers 168 (FIG. 10) in a predetermined intercalated sequence to an analog-to-digital converter 194, the output of which is stored in a computer memory 196 by a sampling circuit 198 of computer 190. A wave analysis module 200 of computer 190 retrieves the digital data from memory 196 and processes the data to determine three dimensional organic structures inside a patient. This three-dimensional structural data is provided to a view selection module 202 for deriving two-dimensional images for display on monitor 158 (FIG. 10). A filter module 204 is provided for removing selected organs from the image presented on the visual display or video monitor 158. Sampling circuit 198, wave analysis module 200, view selection module 202, and filter module 204 are program-modified generic digital circuits of computer 190.

Figure 12:
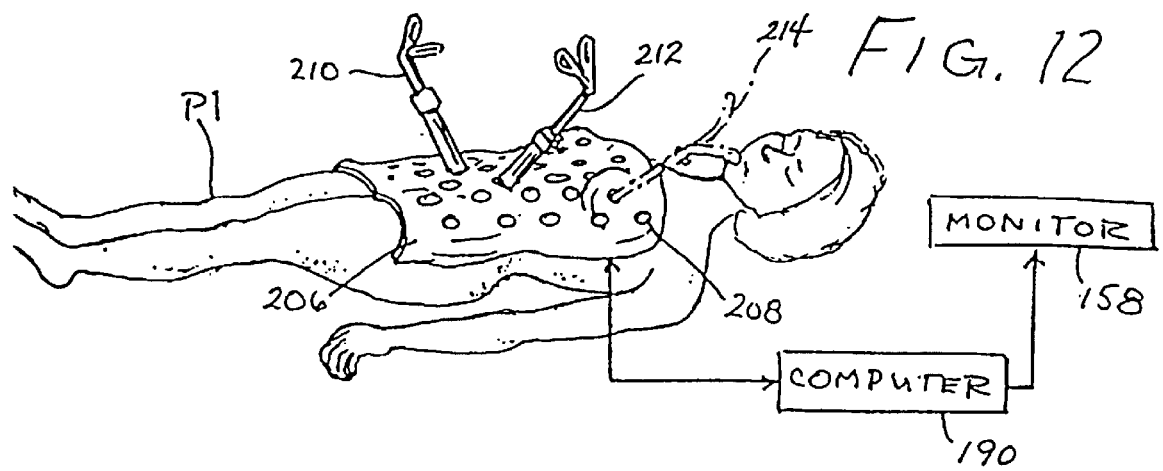
FIG. 12 is partially a schematic perspective view and partially a block diagram showing use of an ultrasonographic imaging device in a minimally invasive diagnostic or therapeutic procedure.

FIG. 12 shows a use of a flexible ultrasonic sensor web 206 which may be any of the flexible ultrasonic sensor webs described herein, except that web 206 is additionally provided with a plurality of apertures or perforations 208. Upon the placement of web 206 in pressure-wave transmitting contact with a skin surface of a patient P, elongate diagnostic or therapeutic instruments such as laparoscopic surgical instruments 210 and 212 are inserted through respective openings 208 to perform a surgical operation on a designated internal organ of the patient P1. This operation is effectuated by viewing a real time image of the distal ends of the instruments 210 and 212 in relation to the patient's internal organic structures as determined by control unit 156 or computer 190. Generally, the image on monitor 158 is viewed during insertion of instruments 210 and 212 to enable a proper employment of those instruments. Also, the video images on monitor 158 are viewed to enable a proper carrying out of the "laparoscopic" surgical operation on the designated internal organ of the patient P1. Strictly speaking, this operation is not a laparoscopic operation, since a laparoscope is not used to provide a continuing image of the patient's internal organic structures and the distal ends of instruments 210 and 212.

There are multiple advantages to using sonographic web 206 instead of a laparoscope. Fewer perforations need be made in the patient for the same number of surgical instruments. In addition, multiple views of the patient's internal organic structures are possible, rather than a single view through a laparoscope. Generally, these multiple views may differ from one another by as little as a few degrees of arc. Also, particularly if web 206 is extended essentially around patient P1, viewing angles may be from under the patient where a laparoscopic could not realistically be inserted.

Web 206 may be used to insert tubular instruments such as catheters and drainage tubes, for example, for thoracentesis and abscess drainage. The tubes or catheters are inserted through apertures 208 under direct real time observation via monitor 158.

In addition to treatment, web 206 may be used to effectuate diagnostic investigations. In particular, a biopsy instrument 214 may be inserted through an aperture 208 to perform a breast biopsy, a liver biopsy, a kidney biopsy, or a pleural biopsy.

Figure 13:
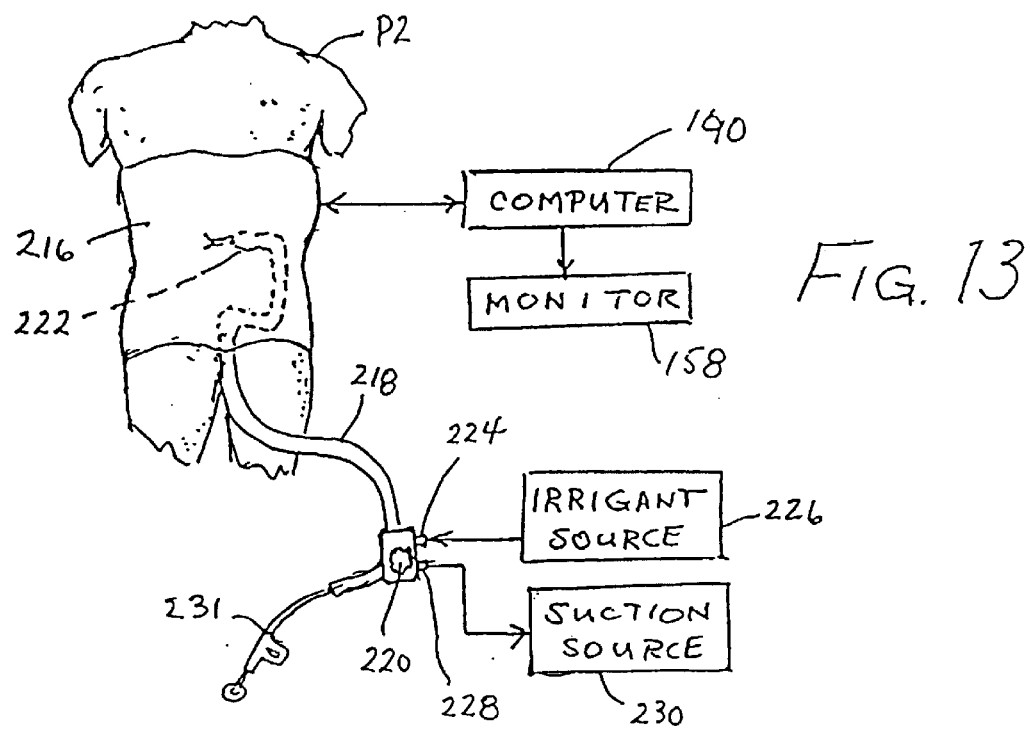
FIG. 13 is a partial schematic perspective view including a block diagram showing use of an ultrasonographic imaging device in another minimally invasive diagnostic or therapeutic procedure.

As illustrated in FIG. 13, a flexible ultrasonic sensor web 216, which may be any of the flexible ultrasonic sensor webs described herein, may be used in a diagnostic or therapeutic operation utilizing a flexible endoscope-like instrument 218. Instrument 218 has a steering control 220 for changing the orientation of a distal tip 222 of the instrument. Instrument 218 also has a port 224 connected to an irrigant source 226 and another port 228 connected to a suction source. In addition, instrument 218 is provided a biopsy channel (not shown) through which an elongate flexible biopsy instrument or surgical instrument 230 is inserted.

Instrument 218 is considerably simplified over a conventional endoscope in that instrument 218 does not require fiber-optic light guides for carrying light energy into a patient P2 and image information out of the patient. Instead, visualization of the internal tissues and organ structures of patient P2 is effectuated via monitor 158 and control unit 156 or computer 190. As discussed above with reference to FIG. 12, the sonographic imaging apparatus if web 216 is extended essentially around patient P2, images may be provided from multiple angles, not merely from the distal tip 222 of instrument 218.

View selector 174 and organ filter stage 176 or view selection module 202 and filter module 204 may function in further ways to facilitate viewing of internal organic structures. In addition to organ removal and highlighting, discussed above, a zoom capability may be provided. The zoom or magnification factor is limited only by the resolution of the imaging, which is determined in part by the frequency of the ultrasonic pressure waves. The resolution of the imaging is also determined by the sizes of various transducer arrays which function together as single apertures. Generally, the larger the array, or the more transducers which are energized or sampled synchronously, then the higher the resolution. As discussed hereinafter with reference to FIG. 29 et seq., coherent aperture combining is used to increase the sizes of the transducer array apertures, thereby maximizing image resolution.

FIGS. 14 and 15 depict a specialized ultrasonic sensor web 232 in the form of a garment such as a vest. Sensor vest 232 has arm holes 234 and 236, a neck opening 238 and fasteners 240 for closing the vest about a patient. In addition, sensor vest 232 is provided with a plurality of elongate chambers 242 which receive fluid for expanding the vest into conformation with a patient's skin surface, thereby ensuring contact of the vest with a patient's skin surface and facilitating the transmission of ultrasonic pressure waves to and from ultrasonic transducers 244. FIG. 14 shows a computer 246, a video monitor 248 and a printer 250 used as described above.

Sensor vest 232 may be understood as a container assembly having fluid-filled chambers 242 with flexible inwardly facing walls (not separately designated) which conform to the patient. Sensor vest 232 may additionally be provided along an inner side with a conventional interface medium, whether water, gel, plastic or some other material, which is conducive to the transmission of ultrasonic vibrations across the interface between the patient and the sensor vest.

Figure 16:
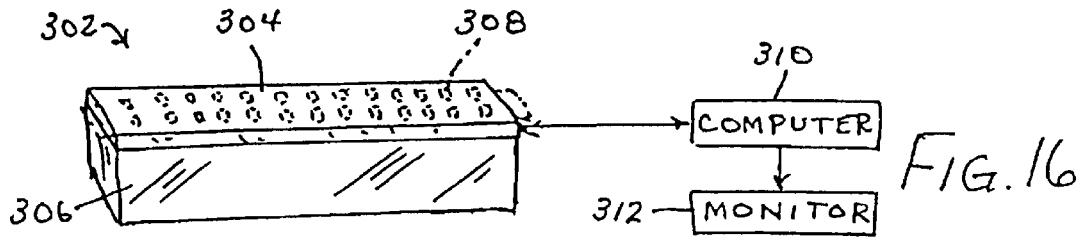
FIG. 16 is partially a schematic perspective view and partially a block diagram of an ultrasonic diagnostic imaging device.
Figure 17:
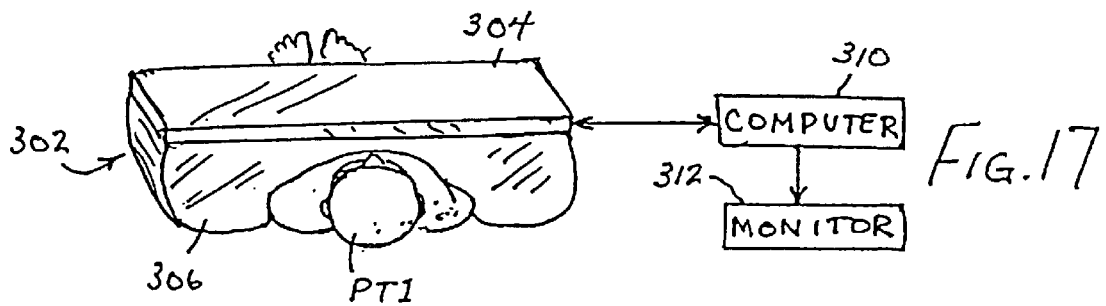
FIG. 17 is partially a schematic perspective view and partially a block diagram of the ultrasonic diagnostic imaging device of FIG. 16, showing the device in use with a patient.

As illustrated in FIG. 16, an ultrasonography apparatus comprises a container assembly 302 including a substantially rigid plate 304 attached to a flexible bladder or bag 306. Bladder or bag 306 is filled with a liquid and is sufficiently flexible to substantially conform to a patient when the container assembly 302 is placed onto a patient PT1, as illustrated in FIG. 17. A liquid or gel or other interface medium may be deposited on the patient prior to the placement of container assembly 302 on patient PT1.

Plate 304 is provided with multiple ultrasonic pressure wave generators and receivers 308 as described above with respect to FIGS. 8 and 9 and FIGS. 14 and 15. Generators and receivers 308 are connected to a computer 310 having essentially the same functional structures and programming as computer 190 for implementing sequential generator energization and sequential receiver sampling, as described above. Computer 310 is connected to a monitor 312 for displaying images of internal organs of patient PT1. Computer 310 has the capability of alternately displaying organ images from different angles, as discussed above.

Ultrasonic pressure wave generators and receivers 308 may be densely packed and energized or interrogated as individual elements separately from each other. Coherent aperture combining is not used in such an operating mode. Alternatively, the ultrasonic pressure wave receivers 308 may be sampled or interrogated in groups, permitting the formation of a plurality of data gathering apertures. In that case, computer 310 may coherently combine structural data from the different apertures to thereby increase focusing power or resolution.

Plate 304 may be formed as a rectangular array of rigid modular substrates rigidly connected to one another, each of the substrates holding a plurality of the transducers. The modular substrates are off-the-shelf components such as the 1.5D transducer arrays found in conventional, premium probes, with on the order of 100 piezoelectric transducers (or elements) disposed in a tightly packed line along a length dimension of the substrate. Inter-element spacing is typically one wavelength or less to support full scanning along the length dimension. A width dimension of a modular substrate carries substantially fewer (e.g. less than 10) piezoelectric transducers. Inter-element spacing along the width dimension is typically a few or several wavelengths. The electronic scanning of internal tissue structures of a patient along the length dimension is performed conventionally by computer 310. Computer 310 also provides electronic scanning of internal tissue structures of a patient in the width dimensions of the modular substrates, where the density of the transducers is low, using a procedure unique to the present invention which is described in detail hereinafter.

Figure 18:
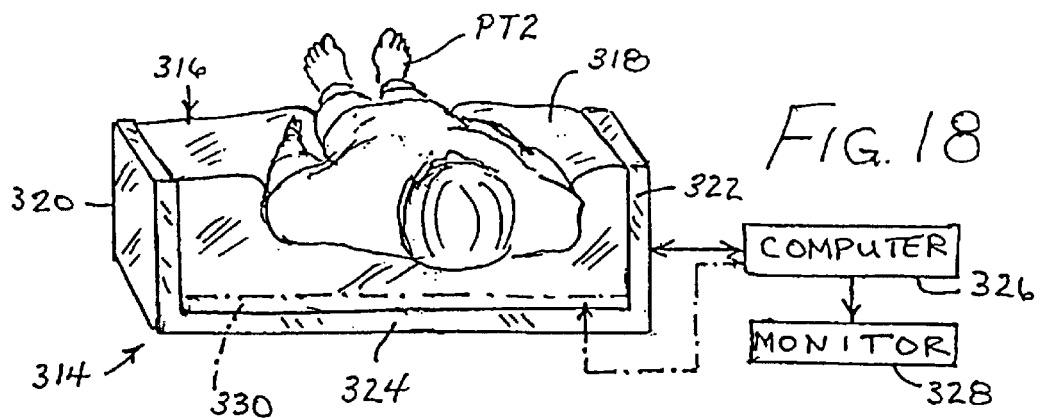
FIG. 18 is partially a schematic perspective view and partially a block diagram of another ultrasonic diagnostic imaging device, showing the device in use with a patient.

FIG. 18 depicts another ultrasonography apparatus useful for both diagnostic investigations and minimally invasive surgical operations. The apparatus comprises a container assembly 314 which includes a fluid-filled sack or bag 316 for receiving a patient PT2. Sack or bag 316 includes a flexible upper wall 318 which deforms to conform to the patient PT2 upon placement of the patient onto the bag. Bag 316 is supported on two or more sides by substantially rigid walls or panels 320 and 322. Panels 320 and 322 are either integral with bag 316 or separable therefrom. Panels 320 and 322, as well as an interconnecting bottom panel 324, may be provided with multiple ultrasonic pressure wave generators and receivers (not shown) as described above with respect to FIGS. 8 and 9, FIGS. 14 and 15, and FIG. 16. These generators and receivers are connected to a computer 326 having essentially the same functional structures and programming as computer 190 for implementing sequential generator energization and sequential receiver sampling, as described above. Computer 326 is connected to a monitor 328 for displaying images of internal organs of patient PT2. Computer 326 has the capability of alternately displaying organ images from different angles, as discussed above.

The ultrasonic pressure wave generators and receivers may be disposed in a wall panel of bag 316 or may be provided in a separate carrier 330 disposable, for example, between bottom panel 324 and bag 316, as shown in FIG. 18.

Where the ultrasonic pressure wave generators and receivers may be densely packed and energized or interrogated as individual elements separately from each other. Coherent aperture combining is not used in such an operating mode. Alternatively, the ultrasonic pressure wave receivers may be sampled or interrogated in groups, permitting the formation of a plurality of data gathering apertures. In that case, computer 326 may coherently combine structural data from the different apertures to thereby increase focusing power or resolution.

Figure 19:
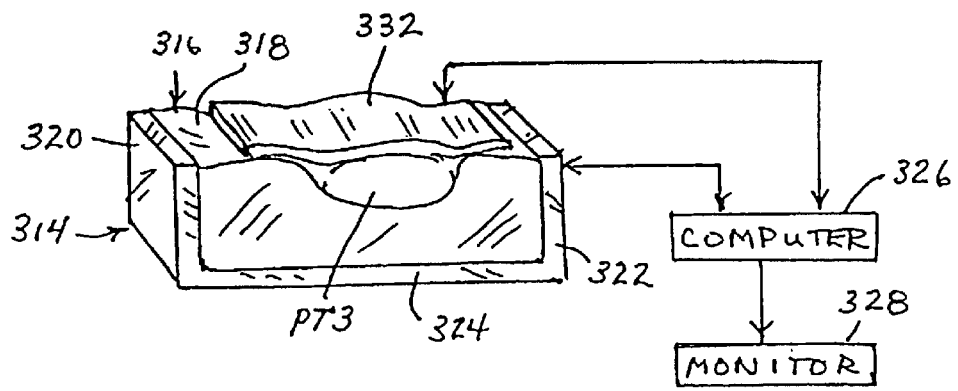
FIG. 19 is partially a schematic perspective view and partially a block diagram of the ultrasonic diagnostic imaging device of FIGS. 17 and 18, showing a modification of the device of those figures.

As illustrated in FIG. 19, the ultrasonography apparatus of FIG. 19 may be used in conjunction with a flexible web or cover sheet 332 identical to web 132, 150, or 206 (FIG. 8, 9, or 12). Web or cover sheet 332 is operatively connected to computer 326 for providing ultrasonically derived organ position and configuration data to the computer for displaying organ images on monitor 328. The use of web or sheet 332 enables the disposition of ultrasonic wave generators and receivers in a 360 arc about a patient PT3 (diagrammatically illustrated in FIG. 19), thereby facilitating image production. Where web or sheet 332 takes the form of web 206, the sheet is provided with apertures (see FIG. 12 and associated description) for enabling the introduction of minimally invasive surgical instruments into the patient PT3.

As discussed above, to contact surfaces a liquid, gel or other conductive medium is applied to facilitate ultrasonic pressure wave transmission over interfaces.

As discussed hereinafter with reference to FIG. 20, video monitor 158 (FIGS. 10, 12, and 13) or monitor 328 (FIG. 19) may take the form of a flexible video screen layer attached to web 132, 150, 166 or 206 (FIGS. 8, 9, 10, 12) or web 332 (FIG. 19). This modification of the ultrasonographic imaging devices discussed above is considered to be particularly advantageous in medical diagnosis and treatment procedures. The web or substrate with the video screen is disposed on a selected body portion of a patient, for example, the abdomen (FIGS. 12 and 21) or a shoulder (FIGS. 22A, 22B) or knee (FIG. 23B), so that the substrate and the video screen layer substantially conform to the selected body portion and so that the video screen is facing away from the body portion.

Figure 20:
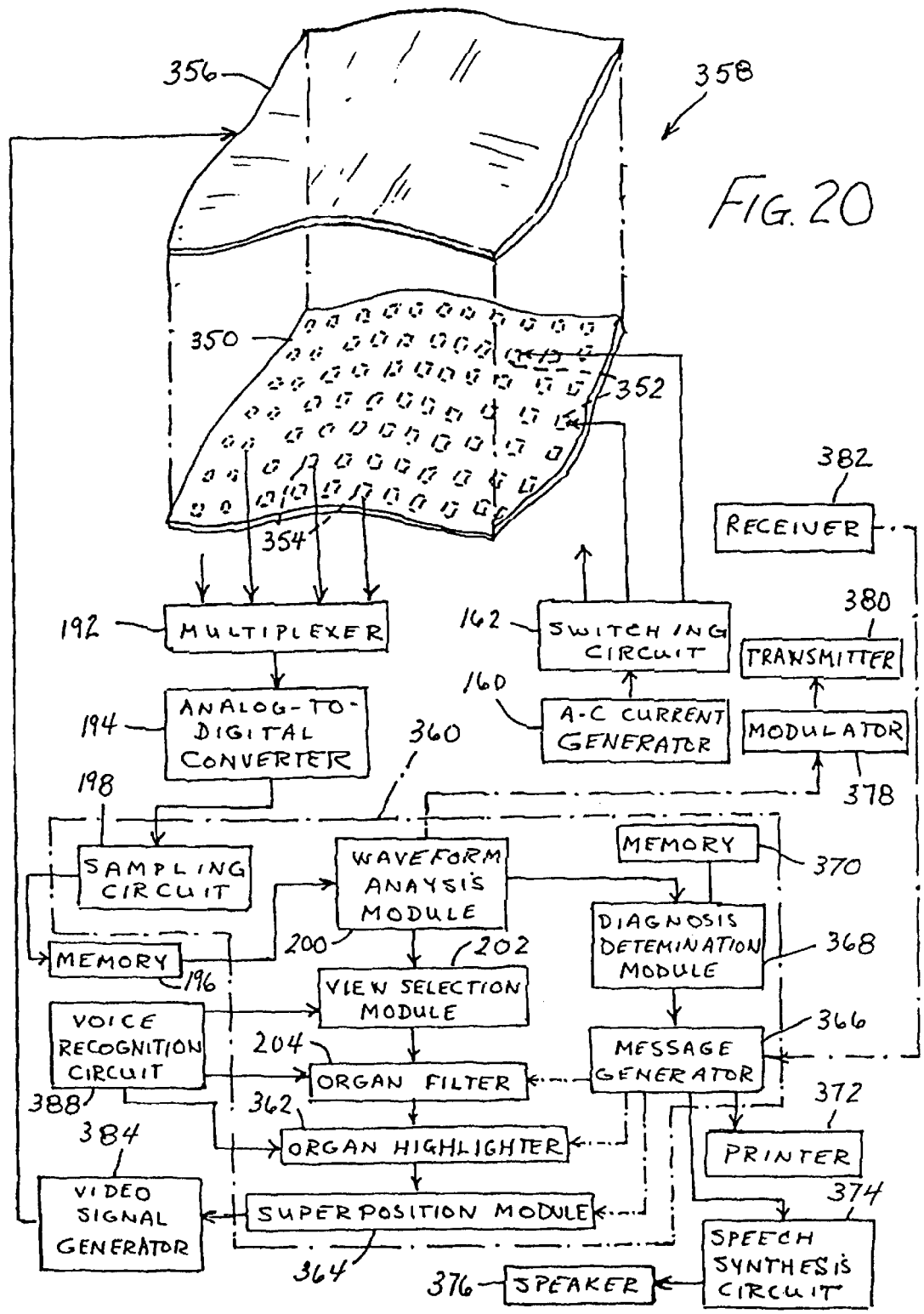
FIG. 20 is partially a schematic exploded perspective view and partially a block diagram of an ultrasonographic device or system related to the present invention.

As shown in FIG. 20, an ultrasonographic device or system comprises a flexible substrate or web 350 which carries a plurality of piezoelectric electroacoustic transducers 352 and a plurality of piezoelectric acoustoelectric transducers (or receivers) 354. A flexible video screen 356 is attached to substrate or web 350 substantially coextensively therewith. Video screen 356 may be implemented by a plurality of laser diodes (not shown) mounted in a planar array to a flexible carrier layer (not separately designated). The diodes are protected by a cover sheet (not separately illustrated) which is connected to the carrier layer. Energization componentry is operatively connected to the diodes for energizing the diodes in accordance with an incoming video signal to reproduce an image embodied in the video signal. In a video monitor, the laser diodes are tuned to different frequency ranges, so as to reproduce the image in color. The protective cover sheet may function also to disperse light emitted by the laser diodes, to generate a more continuous image.

Substrate or web 350 and video screen 356 comprise an ultrasonic video coverlet or blanket 358 which may be used with the control hardware depicted in FIGS. 10 and 11. Reference numerals used in FIGS. 10 and 11 are repeated in FIG. 20 to designate the same functional components.

Electroacoustic transducers 352 are connected to a-c or ultrasonic signal generator 160 for receiving respective a-c signals of variable frequencies. Generator 160 produces frequencies which are directed to the electroacoustic transducers 352 by switching circuit 162. Pressure waveforms of different ultrasonic frequencies have different penetration depths and resolutions and provide enhanced amounts of information to a digital signal processor or computer 360. As discussed above with reference to computer 190 of FIG. 11, computer 360 is a specially programmed digital computer wherein functional modules are realized as generic digital processor circuits operating pursuant to preprogrammed instructions.

As discussed above with reference to FIG. 11, switching circuit or multiplexer 192 relays signals incoming from respective acoustoelectric transducers 354 in a predetermined intercalated sequence to analog-to-digital converter 194, the output of which is stored in computer memory 196 by sampling circuit 198. Acoustoelectric transducers 354 may be interrogated by multiplexer 192 and sampling circuit 198 in such a sequence as to enable or facilitate a grouping of transducers 354 to form a plurality of data gathering apertures. Waveform analysis module 200 retrieves the digital 3D volumetric data from memory 196 and processes the data acquired from the internal tissue structures, thereby determining three dimensional organic structures inside a patient. Waveform analysis module 200 includes coherent aperture combining circuitry (see FIG. 29) for coherently combining structural data from the respective apertures. Wave analysis module 200 also includes position determination circuitry which executes computations according to a self-cohering algorithm that computes the relative positions and orientations of the respective apertures using instantaneous position measurements and adjusts the signals from the coherently combined apertures so they can be added together constructively. Analysis module 200 may also include the option of noncoherently combining structural data, which allows extended images to be created without increasing the imaging resolution.

The three-dimensional structural data generated by waveform analysis module 200 is provided to view selection module 202 for deriving two-dimensional images for display on video screen 256. Filter module 204 serves to remove selected organs, for example, overlying organs, from the image presented on video screen 356. Sampling circuit 198, wave analysis module 200, view selection module 202, and filter module 204 are program-modified generic digital circuits of computer 360.

Computer 360 contains additional functional modules, for example, an organ highlighter 362 and a superposition module 364. The functions of organ highlighter 362 are discussed above with reference to organ filter 176 and 204 in FIGS. 10 and 11. Organ highlighter 362 operates to provide a different color or intensity or cross-hatching to different parts of an image to highlight a selected image feature. For example, a gall bladder or an appendix may be shown with greater contrast than surrounding organs, thereby facilitating perception of the highlighted organ on video screen 356. After organ filter 204 has removed one or more selected organs from an electronic signal representing or encoding an image of internal organs, highlighter 362 operates to highlight one or more features of the encoded image.

Superposition module 364 effects the insertion of words or other symbols on the image displayed on video screen 356. Such words or symbols may, for example, be a diagnosis or alert signal produced by a message generator module 366 of computer 360 in response to a diagnosis automatically performed by a determination module 368 of computer 360. Module 368 receives the processed image information from waveform analysis module 200 and consults an internal memory 370 in a comparison or pattern recognition procedure to determine whether any organ or internal tissue structure of a patient has an abnormal configuration. The detection of such an abnormal configuration may be communicated to the physician by selectively removing organs, by highlighting organs or tissues, or superimposing an alphanumeric message on the displayed image. Accordingly, message generator 366 may be connected to organ filter 204 and organ highlighter 362, as well as to superposition module 364. The communication of an abnormal condition may be alternatively or additionally effectuated by printing a message via a printer 372 or producing an audible message via a speech synthesis circuit 374 and a speaker 376.

As discussed above, the ultrasonically derived three-dimensional structural information from waveform analysis module 200 may be transmitted over a telecommunications link (not shown in FIG. 20) via a modulator 378 and a transmitter 380. The transmitted information may be processed at a remote location, either by a physician or a computer, to generate a diagnosis. This diagnosis may be encoded in an electrical signal and transmitted from the remote location to a receiver 382. Receiver 382 is coupled with message generator module 366, which can communicate the diagnosis or other message as discussed above.

Computer 360 is connected at an output to a video signal generator 384 (which may be incorporated into the computer). Video signal generator 384 inserts horizontal and vertical synchronization signals and transmits the video signal to video screen 356 for displaying an image of internal patient organs thereon.

Figure 21:
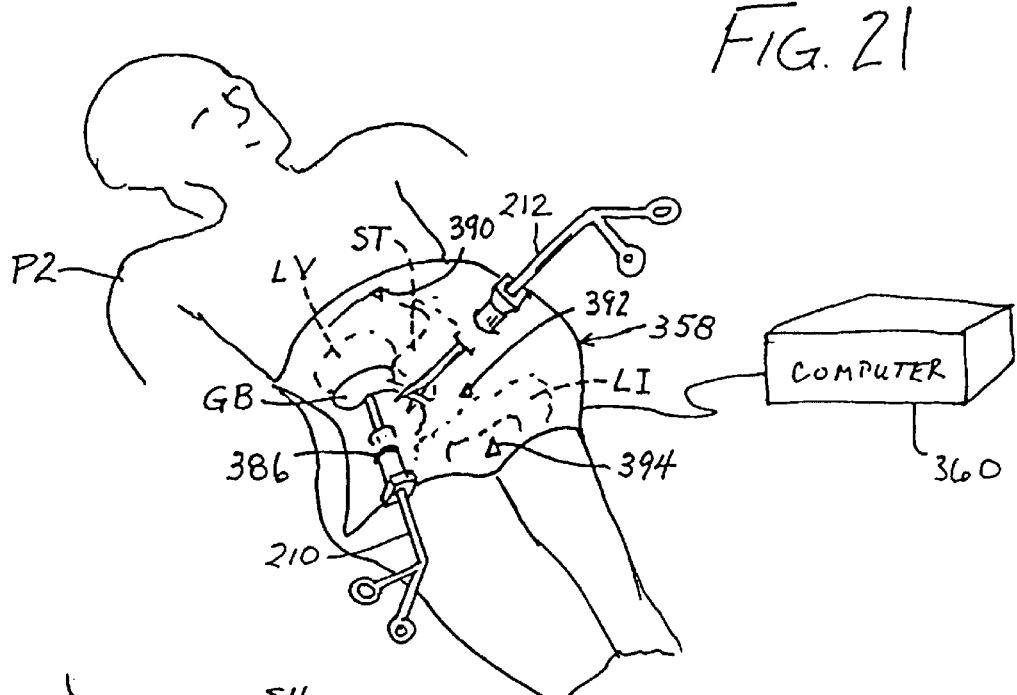
FIG. 21 is a schematic perspective view showing use of the system of FIG. 20 in performing a laparoscopic operation.

FIG. 21 diagrammatically depicts a step in a "laparoscopic" cholecystectomy procedure utilizing the ultrasonographic device or system of FIG. 20. Coverlet or blanket 358 is disposed on the abdomen of a patient P2 in pressure-wave transmitting contact with the skin. The skin is advantageously wetted with liquid to facilitate ultrasonic pressure wave transmission. Laparoscopic surgical instruments 210 and 212 (same as in FIG. 12) are inserted through respective openings 386 in coverlet or blanket 358 to perform a surgical operation on a gall bladder GB of the patient P2. This operation is effectuated by viewing a real time image of the distal ends of the instruments 210 and 212 in relation to the patient's internal organic structures as determined by computer 360. Generally, the image on video screen 356 is viewed during insertion of instruments 210 and 212 to enable a proper employment of those instruments.

As illustrated in FIG. 21, the gall bladder GB is highlighted (e.g., with greater contrast in screen intensities) relative to other organs such as the liver LV, the stomach ST and the large intestine LI. One or more of these organs may be deleted entirely by organ filter 204. Computer 360 is instructed as to the desired display features via a keyboard (not illustrated in FIG. 20) or a voice recognition circuit 388 operatively connected to various modules 202, 204 and 362. (It is to be noted that speech synthesis circuit 374 and voice recognition circuit 388 enable computer 360 to carry on a conversation with a user. Thus the user may direct the computer to answer questions about the appearance of certain organs selected by the user.)

Generally, the images of the different organs GB, LV, ST and LI, etc., are displayed on video screen 356 so as to substantially overlie the actual organs of the patient P2. To effectuate this alignment of image and organ, markers 390, 392, 394 are placed on the patient P2 at appropriate identifiable locations such as the xyphoid, the umbilicus, the pubis, etc. The markers are of a shape and material which are easily detected by ultrasonic wave analysis and provide computer 360 with a reference frame for enabling the alignment of organ images on screen 356 with the corresponding actual organs. During an operation, view selector 202 may be utilized (via keyboard command or voice recognition circuit 388) to adjust the relative positions of image and organs to facilitate the performance of an invasive surgical operation. As discussed above with reference, for example, to FIG. 13, the ultrasonographic device or system of FIG. 20 may be used in other kinds of procedures.

Figure 22A:
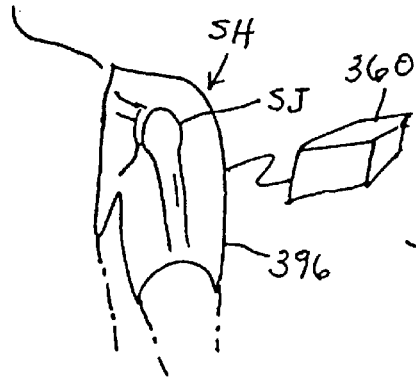
FIGS. 22A and 22B are schematic perspective views showing use of another ultrasonographic device related to the present invention.
Figure 22B:
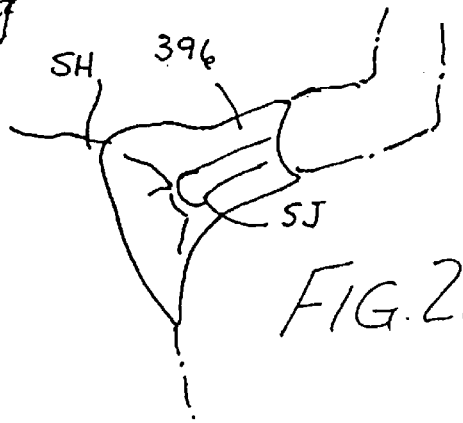

As illustrated in FIG. 22A, an ultrasonographic coverlet or blanket 396 with attached video screen (not separately designated) and connected computer 398 has a predefined shape conforming to a shoulder SH. The coverlet or blanket 396 is flexible and thus deforms upon motion of the shoulder (FIG. 22B). The coverlet or blanket 396 has a memory so that it returns to the predefined shape when it is removed from the shoulder SH. The flexibility of the coverlet or blanket 396 enables the display in real time of a filtered video image showing the shoulder joint SJ during motion of the shoulder. This facilitates a diagnostic appraisal of the joint.

Figure 23A:
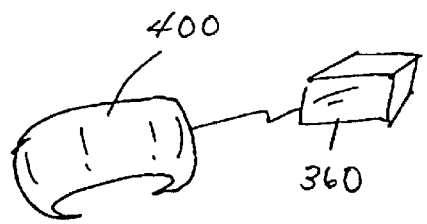
FIG. 23A is a schematic perspective view of a further ultrasonographic device related to the present invention.
Figure 23B:
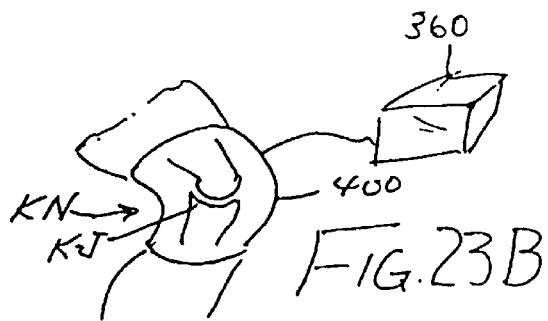
FIG. 23B is a schematic perspective view showing use of the ultrasonographic device of FIG. 23A.

FIG. 23A illustrates an ultrasonic video cuff 400 with a computer 402. The cuff is attachable in pressure-wave transmitting contact to a knee KN, as depicted in FIG. 23B. Cuff 400 conforms to the knee KN and follows the knee during motion thereof. A knee joint KJ is imaged on the cuff during motion of the knee KN, thereby enabling a physician to study the joint structure and function during motion. Cuff 400 has a memory and returns to its predefined shape (FIG. 23A) after removal from knee KN.

Video screen 356, as well as other video monitors disclosed herein, may be a lenticular lens video display for presenting a stereographic image to a viewer. The ultrasonic processor, e.g., computer 190 or 360, operates to display a three-dimensional image of the internal organs on the lenticular lens video display. 118. Because of the stereoscopic visual input a surgeon is provided via video display 356, he or she is better able to manipulate instruments 210 and 212 during a surgical procedure.

Electroacoustic transducers 134, 164, 352 in an ultrasonographic coverlet or blanket 132, 166, 206, 216, 358 as described herein may be used in a therapeutic mode to dissolve clot in the vascular system. The coverlet or blanket is wrapped around the relevant body part of a patient so that the electroacoustic transducers surround a target vein or artery. First, a scan is effectuated to determine the location of the clot. Then, in a clot dissolution step, the electroacoustic transducers are energized to produce ultrasonic pressure waves of frequencies selected to penetrate to the location of the clot. With a sufficiently large number of transducers transmitting waves to the clot site simultaneously, the clot is disrupted and forced away from the clot site. It is recommended that a filter basket be placed in the pertinent blood vessels downstream of the clot site to prevent any large clot masses from being swept into the brain or the lungs where an embolism would be dangerous.

The monitors disclosed herein, such as monitors 158, 248, 312, 328 and video screen 356, may be provided with a lenticular lens array (not shown) for generating a three-dimensional or stereoscopic display image when provided with a suitable dual video signal. Such a dual signal may be generated by the waveform analysis computer 190, 310, 326, 360 with appropriate programmed for the view selection module 202 to select two vantage points spaced by an appropriate distance. Lenticular lens video displays, as well as the operation thereof with input from two cameras, are disclosed in several U.S. patents, including U.S. Pat. No. 4,214,257 to Yamauchi and U.S. Pat. No. 4,164,748 to Nagata, the disclosures of which are hereby incorporated by reference.

It is to be noted that any of the ultrasonography devices or systems disclosed herein may be used in a robotic surgical procedure wherein one or more surgeons are at a remote location relative to the patient. The performance of robotic surgery under the control of the distant experts is disclosed in U.S. Pat. Nos. 5,217,003 and 5,217,453 to Wilk, the disclosures of which are hereby incorporated by reference. Video signals transmitted to the remote location may be generated by the analysis of ultrasonic waves as disclosed herein.

The ultrasonography devices or systems disclosed herein may be used in conjunction with other kinds of scanning devices, for example, spectral diagnosis and treatment devices described in U.S. Pat. Nos. 5,305,748 to Wilk and 5,482,041 to Wilk et al. (those disclosures incorporated by reference herein). It may be possible to incorporate the electromagnetic wave generators and sensors of those spectral diagnosis and treatment devices into the coverlet or blanket of the present invention.

As illustrated in FIG. 24, a medical imaging device comprises a planar firm substrate 404, a substantially flat video screen 406 provided on the substrate, and a flexible bag 408 connected to the substrate. Flexible bag 408 contains a fluidic medium such as water or gel capable of transmitting pressure waves of ultrasonic frequencies and is disposed on a side of the substrate opposite the video screen. Alternatively and equivalently, bag 408 may be a substantially solid mass of a deformable material conducive to the transmission of ultrasonic pressure waves. Certain plastic or polymeric materials known in the art would be suitable for such an application. As discussed above, a scanner 410 including an ultrasonic waveform generator 412 and a computer-implemented ultrasonic signal processor 414 are operatively connected to video screen 406 for providing a video signal thereto. The video signal encodes an image of internal tissues of a patient PT4 upon placement of medium-containing bag 408, substrate 404, and video screen 406 against the patient. The images of internal tissues and organs off the patient, including the stomach SH, the heart HT, the lungs LG, the small intestine SE, and the large intestine LE, are displayed on screen 406 at positions generally overlying the respective actual tissues and organs of the patient PT4.

Video screen 406 and substrate 404 may be provided with aligned apertures 415 for enabling the traversal of the video screen and the substrate by medical instruments as discussed above with reference to FIG. 21.

Figure 27A:
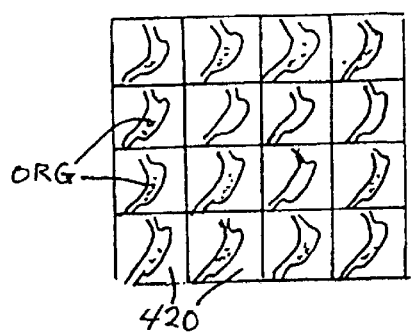
FIG. 27A is a schematic front elevational view of a video screen display configuration utilizable in the ultrasonographic device of FIGS. 25 and 26.

FIGS. 25 and 26 show another medical imaging device comprising a flexible bag 416 containing a fluidic medium such as water or gel. A multiplicity of substantially rigid planar substrates or carrier pads 418 together with respective flat video screens 420 attached thereto are mounted to an upper surface of bag 416. Bag 416 serves in part to movably mount pads 418 with their respective video screens 420 to one another so that the orientations or relative angles of the video screen can be adjusted to conform to a curving surface of a patient PT5, as shown in FIG. 26. Again, a scanner 422 including an ultrasonic waveform generator 424 and a computer-implemented ultrasonic signal processor 426 is operatively connected to video screens 420 for providing respective video signals thereto. The video signals encode respective images of internal tissues of a patient PT5 upon placement of medium-containing bag 416, substrates 418 and video screens 420 against the patient. As illustrated in FIG. 27A, the video images displayed on screen 420 may be substantially the same, with differences in the angle of view of a target organ ORG, depending on the locations and orientations of the respective screens 420. Alternatively, in an enlarged view, a single image of the target organ ORG may be displayed, with each screen 420 displaying only a part of the total image. The technology for implementing these displays over video screens 420 is conventional and well known.

Scanners 410 and 422 are ultrasonic scanners with the same components as other ultrasonic scanners discussed herein, for example, with reference to FIG. 21. Briefly, scanners 410 and 422 each includes a plurality of electroacoustic transducers and a plurality of acoustoelectric transducers disposed in respective arrays in the respective bag 408 or 416 or on substrates 404 and 418 so that ultrasonic pressure waves can travel through the fluidic medium in the respective bag from the electroacoustic transducers and to the acoustoelectric transducers. Computers or processors 414 and 426 analyze incoming digitized ultrasonic sensor signals which are produced in response to ultrasonic pressure waves reflected from various tissue interfaces in the patient PT4 or PT5. From these incoming ultrasonic sensor signals, computers or processors 414 and 426 determine three-dimensional shapes of tissue interfaces and organs inside the patient PT4 or PT5.

Accordingly, scanners 410 and 422 include electromechanical transducers, specifically electroacoustic and acoustoelectric transducers (neither shown), as discussed herein for generating ultrasonic pressure waves and receiving or detecting reflected pressure waves as discussed hereinabove. The transducers may be mounted to carrier plates or substrates 404 and 418, may be incorporated into flexible bags 408 and 416, or may be disposed in carrier panels underlying the patient as described hereinabove with reference to FIGS. 18 and 19. As discussed below with reference to FIG. 29 et seq., the transducers are possibly incorporated into rigid arrays functioning as respective apertures whose signal outputs may be coherently combined to maximize resolution.

The transducers of scanners 410 and 422 may be densely packed in both length and width dimensions using inter-element spacings, in both the length and width dimensions, of a wavelength or less to support full 2D scanning. Alternatively, presently available, off-the-shelf 1D or 1.5D array technology may be used. Processors 414 and 426 may organize the transducers contained within substrates 404 and 418 into groups or data gathering apertures and coherently combine structural data from the apertures, using CAC, to enhance the attainable resolution. A self-cohering algorithm is not needed in this case since all aperture locations and orientations are known. Within each data gathering aperture, electronic scanning is effectuated to interrogate tissue structures. For the case where data gathering apertures are to be combined from different substrates, a self-cohering algorithm is needed to process the data from the respective apertures in the embodiment of FIGS. 25 and 26.

As discussed above with reference to FIG. 21, it is recommended that markers be placed in prespecified locations on the patient to enable or facilitate an alignment of the displayed tissue representations and the respective underlying actual tissues. The markers are easily recognized by computer 426 and serve to define a reference frame whereby the positions and the orientations of the multiple video screens 420 relative to the patient's internal tissues are detectable. Thus, the position and the orientation of each video screen 420 relative to the internal tissues and organs of the patient PT5 are determined to enable the display on the video screens 420 of images of selected target tissues of the patient. The reference markers facilitate the display on screens 420 of respective views of the same organ or tissues from different angles depending on the positions and orientations of the various screens 420.

As discussed above, for example, with reference to FIGS. 20 and 21, computers or processor 414 and 426 may include a module 362, typically realized as a programmed general computer circuit, for highlighting a selected feature of the internal organs of patient PT4 or PT5. The highlighting is achievable by modifying the color or intensity of the selected feature relative to the other features in the displayed image, thus providing a visual contrast of the selected feature with respect to the other features of the displayed image. An intensity change may be effectuated by essentially blacking or whiting out the other portions of the image so that the selected feature is the only object displayed on the video screen.

The imaging devices of FIGS. 24 and 26 are optionally provided with a voice-recognition circuit 388 and a speech synthesis circuit 374 (FIG. 20) operatively connected to computer or processor 414 and 426. Advantages and uses of these components are discussed above with reference to FIG. 20. As further described above, computers or processors 414 and 426 are possibly programmed for automated diagnosis based on pattern recognition, with the computed diagnosis being communicated to the user physicians via speech synthesis circuit 374.

Figure 27B:
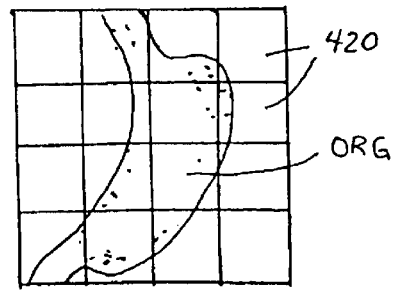
FIG. 27B is a schematic front elevational view of a further video screen display configuration utilizable in the ultrasonographic device of FIGS. 25 and 26.
Figure 28:
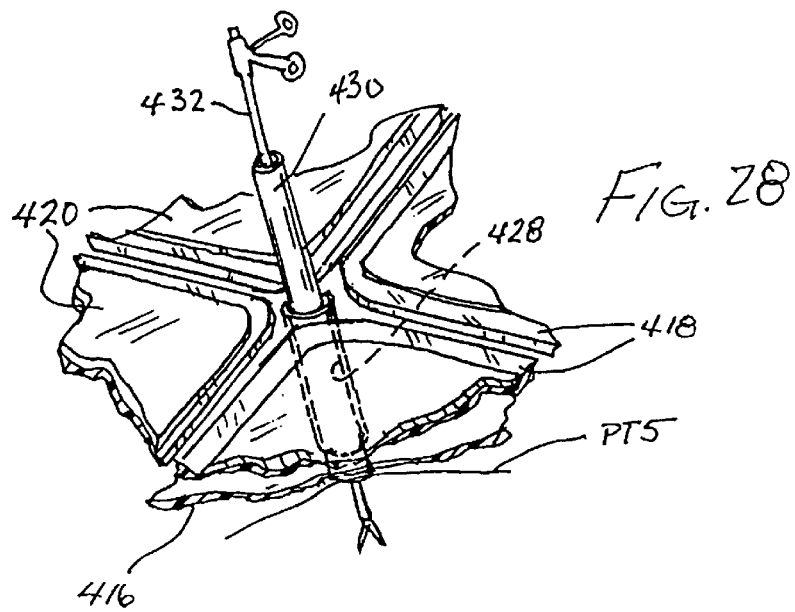
FIG. 28 is a schematic partial perspective view of a modification of the ultrasonographic device of FIGS. 25 and 26, showing a mode of use of the device in a surgical treatment or a diagnostic procedure.

As illustrated in FIG. 28, the imaging device of FIGS. 26 and 27 is advantageously provided with a plurality of apertures or passageways 428 extending through bag 416 in the interstitial spaces between video screens 420. Passageways 428 receive respective tubular cannulas 430 which extend both through the passageways and respective openings (not shown) in the skin and abdominal wall of the patient PT5. Medical instruments such as a laparoscopic forceps 432 are inserted through passageways 428 for performing an operation on internal target tissues of patient PT5 essentially under direct observation as afforded by video screens 420. The distal ends of the medical instruments 432, inserted into patient PT5 in the field of view of the imaging system, are displayed on one or more video screens 420 together with internal target tissues of the patient. The uses of the imaging device of FIGS. 25 and 26 with passageways 428 as illustrated in FIG. 28 are substantially identical to the uses and modes of operation described above with reference to FIGS. 20 and 21.

It is to be noted that bag 416 may be replaced by a plurality of bags (not illustrated) all filled with a fluidic medium through which ultrasonic pressure waves may be transmitted. Each planar substrate or carrier pad 418 and its respective video screen may be attached to a respective fluid-filled bag. In this modification of the ultrasonographic device of FIGS. 25 and 26, apertures performing the function of passageways 428 (FIG. 28) are naturally formed as gaps or spaces between adjacent bags. Separate coupling elements (not illustrated) must be provided between adjacent video screens 420 for forming an integral structure while enabling at least limited flexing between adjacent video screens 420.

It is to be additionally understood that substrates 418 may be formed as carrier layers for active picture elements of video screens 420 and may be visually indistinguishable from the video screens 420.

The imaging devices of FIGS. 24 and 25, 26 may include a transmitter 380 and a receiver 382 (FIG. 20) for operatively connecting scanners 410 and 422 and particularly computers or processors 414 and 426 to a long-distance hard-wired or wireless telecommunications link. As pointed out above, image data transmitted over the telecommunications link to a video monitor at a remote location will enable observation of the patient's internal tissues by distant specialists who may also operate on the patients robotically via the telecommunications link.

Where the imaging device of FIGS. 25-28 is used to diagnose or treat a limb or a joint, planar substrates 418 and video screens 420 have sizes and two-dimensional shapes which facilitate substantial conformity with the limb or joint. To facilitate the use of the imaging device in invasive surgical procedures, the images provided on video screens 420 may be stereoscopic or holographic. Thus, manipulation of medical instrument 432 so that its distal end engages desired internal tissues is facilitated. The imaging device thus may include elements for providing a stereoscopic or holographic image to a viewer, the scanner including means for energizing the elements to produce the stereoscopic or holographic image.

As illustrated in FIG. 29, another ultrasonic imaging system comprises a flexible substrate or web 434 carrying a plurality of modular off-the-shelf transducer packages 436 disposed in a substantially rectangular array. Each package 436 comprises a rigid substrate 437 to which is mounted a multiplicity of piezoelectric crystal transducer elements 438. Transducer elements 438 are all electromechanical and may be termed "electroacoustic" in the case of excitation or transmission of ultrasonic pulses and "acoustoelectric" in the case of reception or sensing of a reflected ultrasonic pulses. Transducer packages 436 may incorporate an arrangement of one or more off-the-shelf hardware components such as conventional 1D and 1.5D arrays as described elsewhere herein, or may be made up of an arrangement (e.g. a 1D or 2D array) of scalar transducer elements.

As discussed above, web 434 may be provided with or on a fluid-filled flexible bag (not shown) for enhancing ultrasonic coupling with a curved surface such as a patient. Other measures may be utilized for facilitating ultrasonic pressure wave transmission from and to the transducer elements 438 of the various modular transducer packages 436.

Generally, it is contemplated that the piezoelectric crystal elements 438 of any given package 436 are energized simultaneously in excitation and reception to effectuate the scanning of an acoustic beam used to interrogate the desired tissue. Thus, each transducer package 436 functions as a single data gathering aperture. The purpose of this technique is to enhance image resolution over currently available 1D and 1.5D array transducers, and to provide electronic 3D volumetric data acquisition. Further enhancement is achieved by coherent aperture combining, discussed below.

Piezoelectric crystal elements 438 are energized by ultrasonic electrical excitation waveforms produced by a signal generator 440 in response to signals from an acquisition controller 442. (Data transmission paths are indicated in FIG. 29 by solid line arrows, while control signal links are indicated in dot-dash lines.) The excitation waveforms from signal generator 440 are directed to selected packages or apertures 436 by a switching circuit or multiplexer 444 in response to control signals from acquisition controller 442. The excitation waveforms are of variable frequency, determined on a continuing basis by acquisition controller 442 and more particularly by a frequency determination module 476 thereof, for optimizing image resolution at different depths (range) into the patient (for example, to obtain a uniform resolution along all coordinate axes). Generally, the higher the frequency, the greater the depth or penetration of effective data acquisition.

The excitation waveforms are generally transmitted as single pulses of short duration, or bursts of several pulses sent and received one after the other. Any one pulse may be directed to a single package or aperture 436 (single aperture excitation) or to multiple packages or apertures 436 simultaneously (multiple aperture excitation). Similarly, signal reception may occur using a single aperture at a given time, or using multiple apertures simultaneously.

Multiplexer 444 is connected to a receiver 446 and is responsive to acquisition controller 442 for selectively connecting the transducer elements 438 of packages or apertures 436 to the signal generator and the receiver. Receiver 446 dynamically focuses incoming signals to produce a number of vectors (range lines) of image data. To that end, receiver 446 incorporates demodulation circuits (not separately shown) to obtain coherently the received signals. It is to be noted that multiplexer 444 may be disposed in whole or in part on web 434. Alternatively, the multiplexer may be located at a workstation.

When different packages (or sets of packages) are used for transmission and reception, the operating mode is termed "bistatic operation." When the same package (or set of packages) is used for transmission and reception, the operating mode is termed "monostatic operation."

The coherent aperture combining module 488 can be used to increase the effective size of the data gathering apertures employed, thereby increasing image resolution. CAC can be performed using monostatic or bistatic operation. For bistatic operation, a given pulse is transmitted, for example, from one aperture, and received simultaneously from two (or more) apertures. The transmit aperture could be one of the two (or more) apertures used for reception. The receiver 446 processes the signals received from both apertures and produces two respective, complex output images. For monostatic operation, two (or more) pulses are needed. On pulse one, aperture one is used for transmission and reception. On pulse two, aperture two is used for transmission and reception. In this case, the receiver 446 produces two respective complex output images, but they pertain to two different times (i.e. the two times associated with the two pulses). The monostatic operating mode has the disadvantage of possible phase shifts in data received by the second transducer array or aperture, as compared with data received by the first transducer array or aperture, due to a different tissue scattering geometry, and different data collection times.

The coherent aperture combining module 448 provides its coherently combined data to an image processor 450.

Image processor 450 utilizes the increased resolution data from module 448 (if CAC is performed) to perform 3D image processing, which includes, as special cases, 1D and 2D image processing as well. 3D image processing can be used to construct three-dimensional models or analogs of internal tissue structures of a patient during a real time scanning operation. As discussed above with reference to other embodiments of an ultrasonic imaging system, an image is constructed by image processor 450 pursuant to instructions entered by a user via a keyboard 452 or other input device and received by a command and control unit 454. The constructed image is displayed on a monitor 456 by command and control unit 454.

During a diagnostic or treatment procedure utilizing the system of FIG. 29, a user requests an image of a particular organ via input device or keyboard 452. Command and control unit 454 interprets the request and relays the interpreted request to acquisition controller 442. Controller 422 queries image processor 450 to determine whether an image of the requested organ is already stored in an internal memory (not shown) of the image processor. If the data is already obtained or is obtainable via interpolation, image processor 450 constructs the requested image, which is then passed to monitor 456 via command and control unit 454. If the data required for imaging the requested organ is not in memory, acquisition controller 442 determines which transducer packages or apertures 436 must be excited and which transducer apertures 436 must be used for reception in order to obtain sufficiently high resolution data to form an image of the requested organ structure. Pursuant to its determination, acquisition controller 442 activates signal generator 440, multiplexer 444, and receiver 446 to implement the acquisition of the requisite data. Prior to data collection, acquisition controller 442 accesses a calibration unit 458 to determine whether a calibration sequence is needed. If so, acquisition controller 442 activates signal generator 440, multiplexer 444 and receiver 446 to conduct an ultrasonic scan for purposes of determining the locations and orientations of the various packages or apertures 436 relative to each other.

Calibration is effectuated by one or both of two techniques. The first technique utilizes acoustic point scatterers 460 (FIG. 30) such as AIUM phantoms disposed on packages or apertures 436. Basically, transducer packages or apertures 436 are activated under the control of acquisition controller 442 to obtain position data on the various point scatterers 460, while module 448 executes a self-cohering algorithm to determine the exact relative positions of the point scatterers, thereby determining the locations and orientations of substrates 437. It is contemplated that phantoms could be embedded in web 434 so that a sufficient number of point scatterers are always in the image field of the group of apertures requiring registration. The calibration data may be acquired bistatically (using a single pulse) or monostatically (using two or more pulses), as described above.

Figure 31:
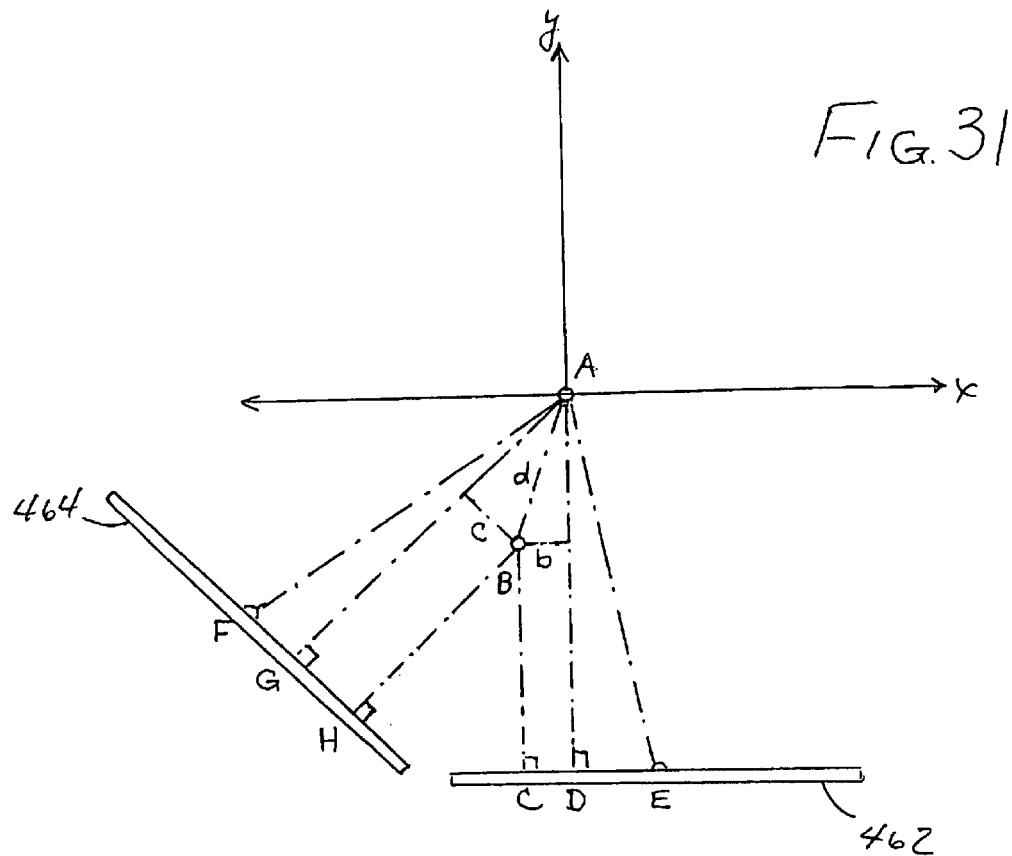
FIG. 31 is a diagram of two relative spaced and rotated modular transducer packages or array apertures similar to that of FIG. 30, showing geometric parameters in a calculation of relative position and orientation.

FIG. 31 is a diagram illustrating geometric parameters in the first calibration technique. Two point scatterers or AIUM phantoms are located at points A and B while transducer arrays or apertures 462 and 464 are centered at points E and F. Transducer array or aperture 464 is rotated through an angle EAF and translated a distance AF-AE from the position of transducer 462. To register transducer 464, it is necessary to determine angle EAF and distances AF and AE.

Distances FG, FH, GA, and HB are measured from data produced by transducer array or aperture 464, while distances ED, EC, DA, and CB are measured using data generated via transducer array or aperture 462. Lengths b, c, and d are easily calculated next. Then, angle DAG is computed. Subsequently, angles EAD and GAF and lengths AE and AF are determined. Angle EAF equals angle EAD plus angle DAG plus angle GAF. (EAF=EAD+DAG+GAF.) The key to these computations is to recognize that the length of the vector joining two point scatterers is invariant under coordinate system translations and rotations and hence will be measured the same from both transducer array or apertures 462 and 464.

Assuming significant signal-to-noise ratios, the cross-range measurements are as good as the apertures can provide, i.e., one picks the vector position where each point scatterer has maximum intensity. Azimuthal centroiding can be used to further improve the cross-range accuracy, depending on the size and orientation of the point scatterers relative to the cross-range resolution of the arrays. To obtain suitable coherent aperture combining results, the range measurements need to be accurate to the array focusing precision, which is better than 10 microns for premium systems. With sufficient signal-to-noise ratios, such accuracies can be achieved by range over sampling (i.e., using the highest A/D sampling rate available) combined with range centroiding techniques. In addition, the point scatterers could also be fabricated in pairs (or triplets, etc.) so that their separations are precisely known, which will assist in making the resulting positioning information more accurate.

Pursuant to the second calibration technique, a direct-path self-cohering algorithm is used. A calibration or reference array or aperture receives a pulsed signal from two or more arrays, whose positions and orientations are to be calibrated relative to each other. The reference array is disposed generally on one side of a patient's body while the arrays to be calibrated are disposed on another side of the body. In a given transverse plane through the patient and a circumferentially extending array of transducer apertures 436, the locations of two points on each array are needed to position and orient the array. (In a more general procedure, the locations of three points on each transducer must be determined.) Solving for the position of a given point on a given array is a triangulation process using two half apertures of the reference array. The two points (or phase centers) on each array correspond to two sub-apertures with a high enough F# in azimuth and elevation to ensure that the calibration array is in the image field. Let each sub-aperture transmit a pulse (or two pulses in sequence if array element access is not available) and let the calibration array receive and process the pulse(s) in each of the two sub-apertures. By measuring the range difference between the two, the position of the array point can be computed relative to the reference array. It is to be noted that this description assumes that the reference array and the arrays to be calibrated are nominally in the same elevation plane. The process is repeated for all transducer arrays or apertures 436 that are to be positioned relative to each other. If all of the arrays in the plane are to be calibrated, then different arrays take turns being the calibration array. Having multiple calibration arrays also allows estimates from different calibration arrays to be averaged, perhaps making the process more robust to deviations from planarity.

Accordingly, in the second calibration technique, the positions of a plurality of preselected phase centres (associated with subapertures formed using a number of transducer elements 438) are determined for each package or aperture 436 required to image the requested organ structure, thereby specifying the location and orientation of those requisite packages or apertures 436. The preselected phase centres are sequentially or separately energized with at least one pulse of a predetermined frequency. At least one preselected transducer array, package or aperture 436 is then polled or sampled using two half-apertures to sense incoming ultrasonic pressure waves of the predetermined frequency transmitted directly (unreflected, although perhaps refracted) through the internal tissues of the patient. Of course, bistatic operation and access to individual transducer elements in an array (i.e. to form the two half-apertures) are required for this calibration procedure to work. The array element access requirement could be eliminated by building reference arrays that consist of two elements joined rigidly (i.e., with known, fixed separation).

The calibration procedure may be performed at regular intervals, with a periodicity determined inter alia by such factors as the target region in the patient, the purpose of the imaging process, and the processing capacity of image processor 450. For example, image data collection for a target region in or near the heart should be updated more frequently than image data collection for a target region in a quiescent limb. Generally, therapeutic invasions require continuous monitoring to a higher degree than diagnostic procedures.

It is to be noted that calibration may alternatively be effectuated by an auxiliary or external sensing system different from transducer arrays or apertures 436. These alternative registration systems are not considered germane to the present invention and are not considered herein.

Coherent aperture combining as implemented by module 448 is an application of techniques known in the transmission and reception of wireless signals, including electromagnetic radiation of various frequencies, as in the field of radar. Antenna array principles are straightforwardly applied to a medical imaging system in order to improve the spatial resolution provided by extant ultrasound array apertures. In general, the larger the combined aperture, the better the lateral resolution.

The ultrasonic imaging systems disclosed herein include appropriate hardware and software (not illustrated) for signal amplification, analog-to-digital conversion, and focusing. The advantageousness of these functions, as well as the elements required to perform these functions, are well known in the conventional ultrasound arts and are not belabored herein.

Figure 32:
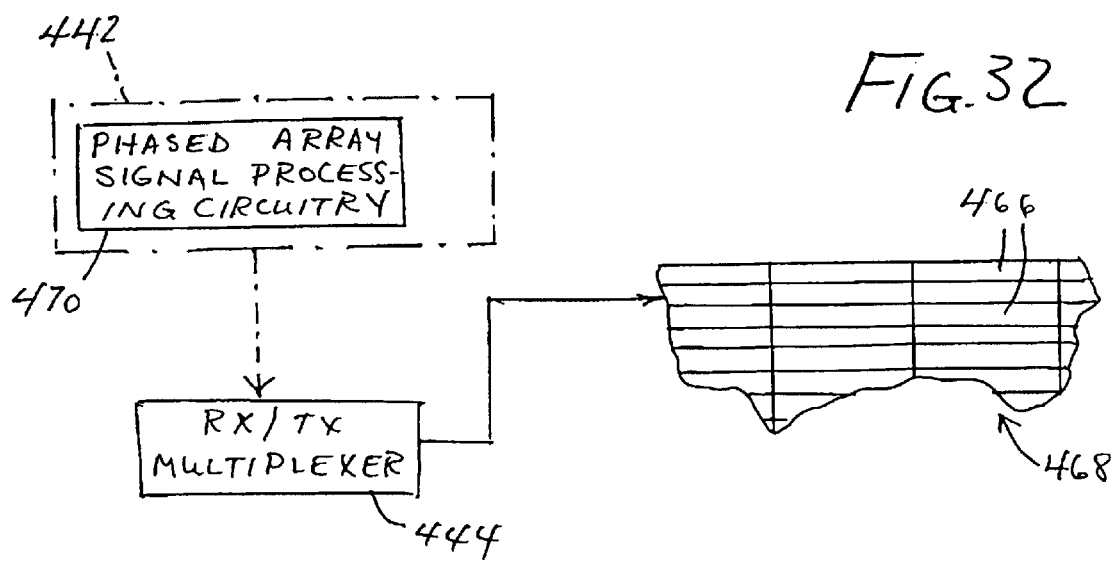
FIG. 32 is partially a schematic perspective view and partially a block diagram showing a modification of the ultrasonic imaging system of FIG. 29.

FIG. 32 depicts transducer hardware which can be used in place of or as a component of web 434 of FIG. 29. A multiplicity of off-the-shelf transducer packages or apertures 466 are rigidly connected to each other in a rectangular array to form an ultrasonic sensor platen 468. This platen or transducer carrier 468 can be used as a component in any of the systems described above. More particularly, the platen can be used as a component in the construction of web 206 in FIG. 12, web 216 in FIG. 13, sensor web 232 in FIGS. 14-15, plate 304 in FIGS. 16-17, panels 320, 322 and 324 in FIGS. 18-19, cover sheet 332 in FIG. 19, web 350 in FIG. 20, blanket 358 in FIG. 21, blanket 396 in FIG. 22A, cuff 400 in FIG. 23A and FIG. 23B, substrate 404 in FIG. 24 and substrates 418 in FIGS. 25-26. Pursuant to some of those systems, platen or transducer carrier 468 is provided with a fluid-filled flexible bag (e.g. 306 in FIG. 18; 316 in FIGS. 18 and 19) disposable in contact with the patient for facilitating transmission of pressure waves into the patient from transducer packages or apertures 466 and transmission of reflected pressure waves from the patient to receiving transducer packages or apertures 466.

The transducer packages 466 (in platen 468) use 1.5D transducer array technology found in conventional, premium probes. This technology employs piezoelectric crystal elements (not shown) whose size along the length dimension is one-wavelength or less, whereas, the size along the width dimension is typically several wavelengths. Each transducer package 466 contains on the order of 100 elements, tightly packed, along the length (or azimuth) dimension, and only a few (usually less than 10) elements, also tightly packed, along the width (or elevation) dimension. Due to the fine spacing along the length dimension, each transducer package can be electronically scanned in azimuth; however, in a conventional probe, no scanning is performed in elevation. A unique feature of the present invention is the ability of platen 468 to scan in elevation as well as azimuth using conventional transducer element technology as described above.

While full 2D electronic scanning is well understood if the transducer elements are one-wavelength or less in both the length and width dimensions (and in which case many, many more elements will be needed to tightly pack a specified-size, 2D platen, and similarly, many more receiver channels will also be required, adding dramatically to the cost and practicality of such a platen), 2D scanning using transducer elements whose feature size is large in the width dimension (as is used herein) is not understood and a unique approach is described below in support of the present invention. As described above, electronic scanning (using phased-array signal processing circuitry) is confined to a data gathering aperture. Platen 468 can be organized into one or more data gathering apertures where each data gathering aperture is capable of 2D scanning; and hence, provides electronic 3D volumetric data acquisition of the tissue structures in the imaging field (i.e. below the skin surface in acoustic contact with the aperture). The acquisition controller 442 (FIG. 29) is provided with phased-array signal processing circuitry 470 for effectuating the 2D electronic scanning of the internal tissue structures associated with each data gathering aperture.

Figure 33:
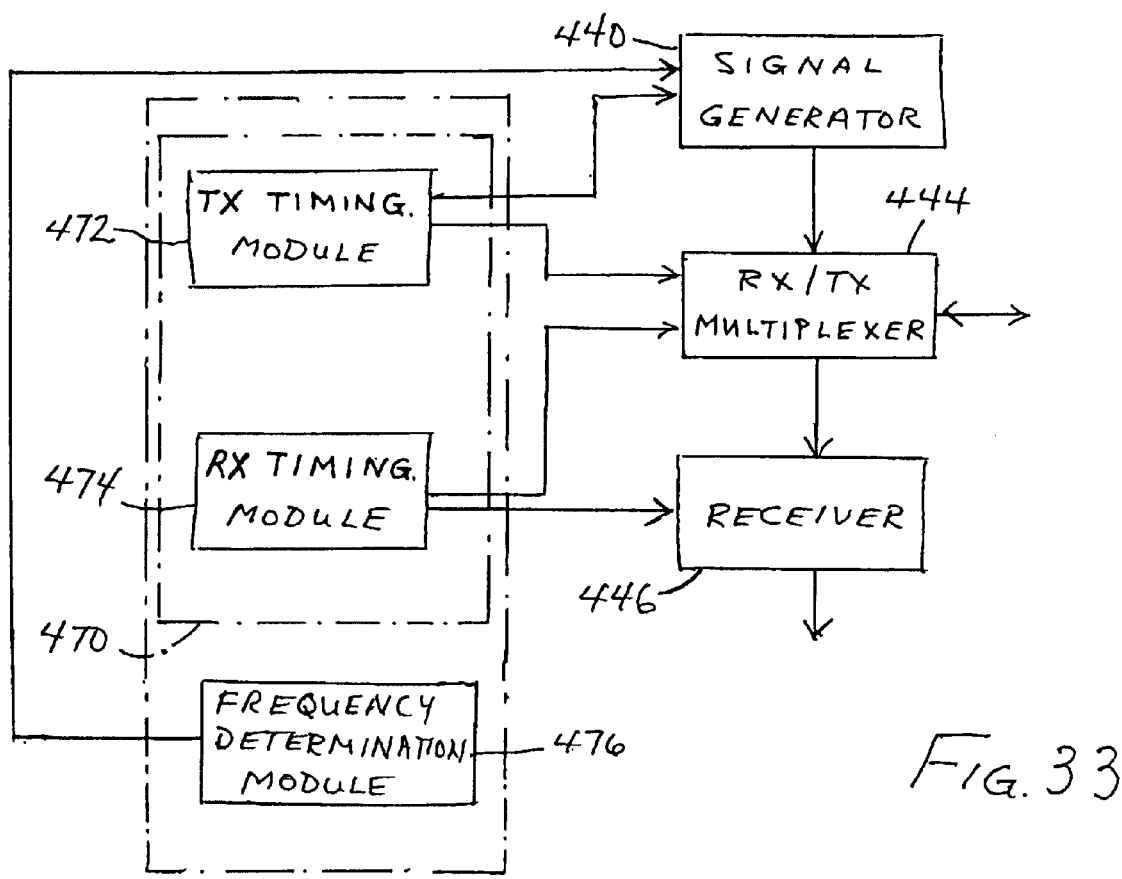
FIG. 33 is a block diagram of components of a phased-array signal processing circuit shown in FIG. 32, also showing components from FIG. 29.

As illustrated in FIG. 33, phased-array signal processing circuitry 470 includes a TX timing module 472 operatively connected to multiplexer or switching circuit 444 for calculating a set of time delays or phases of electrical signals to be sent to the different transducer packages or apertures 466 to effectuate a 2D electronic scan of internal tissue structures of a patient by outgoing pressure waves (i.e. on transmission). The multiplexer or switching circuit 444 imparts the time delays or phases so computed. Thus, the variations in the time delays or phases of electrical signals sent to the different transducer packages or apertures 466 is effectuated in part by multiplexer or switching circuitry 444 under the control of acquisition controller 442 and more particularly in response to control signals from module 472 of phased-array signal processing circuitry 470.

As further illustrated in FIG. 33, phased-array signal processing circuitry 470 further includes an RX timing module 474 operatively connected to multiplexer 444 and receiver 446 and which computes time delays or phases to be used to for effectuating a 2D electronic scanning of incoming reflected pressure waves by transducer packages or apertures 466. The application of the computed time delays or phases to the received signals is typically performed in the receiver 446 although it could be distributed between the multiplexer 444 and the receiver 446.

The phased-array signal processing circuitry 470 performs azimuth (i.e. in the length dimension) electronic scanning in a conventional-like manner. If a data gathering aperture employs a single, off-the-shelf, transducer array, then azimuth scanning (using sequential scanning techniques for a linear array or phased-array scanning for a phased-array) is performed conventionally. If two or more transducer arrays make up the length dimension of the data gathering aperture to form a larger effective aperture, then a straightforward extension of conventional azimuth scanning is applied so that the signals received from each transducer array can be coherently added (in the multiplexer 444 or receiver 446) to effect scanning from the larger effective aperture. If scalar transducer elements are employed in the platen 468 rather than transducer arrays, again, a straightforward application of conventional azimuth scanning techniques can be applied to effectuate azimuth scanning because the locations of all scalar elements are known.

The phased-array signal processing circuitry 470 performs elevation (i.e. in the width dimension) electronic scanning in a non-conventional manner, although conventional principles are applied in terms of the beam focussing techniques used to focus a given voxel (i.e. the image location in the 3D volumetric region being interrogated). This elevation scanning will now be described using as an example the case where the transducer packages 466 used in platen 468 are 1.5D array substrates, each containing on the order of 100 elements in the length dimension, and say seven elements in the width. In practice, elevation scanning is not performed with probes containing 1.5D arrays. A typical probe may have a width dimension of say 1 cm and a length dimension of say 4 cm. When the probe is at a given location, an image slice can be acquired which is typically about 1 mm thick in the elevation or width dimension, and 4 cm long in the azimuth or length dimension. The length of the slice in the depth dimension, D cm, relates to the depth interval in the tissue that is being interrogated. The 1 mm thick image slice is moved manually by the operator's hand in the elevation dimension. That is, the operator manipulates the probe by moving it in the elevation dimension, which in turn moves the image slice in a continuous fashion in the elevation dimension. Consider now the case where platen 468 contains four 1 cm by 4 cm array substrates stacked in the width dimension so that the platen dimension is 4 cm by 4 cm, and assume that a single data gathering aperture is formed from the four substrates contained within the platen. If conventional scanning techniques are applied independently to each substrate, then four 1 mm by 4 cm by D cm image slices can be obtained. Although these slices do indeed span a volume (i.e. one could argue that electronic 3D data acquisition is provided), the volume is not useful in practice because there are large gaps (i.e. 9 mm in width) of volumetric data that are missing between adjacent substrates. Whereas the total spanned volume is 4 cm×4 cm by D cm, only 10% of that volume can be electronically acquired. Although individual substrates cannot electronically scan a full set of scanning angles in the elevation dimension due to the large size of the width dimension of the scalar transducer elements (i.e. several wavelengths), a small amount of electronic scanning, as much as +/−10 deg., is achievable (although not needed nor used in practice with 1.5D probes) without suffering grating lobes or reduction in gain due to the directivity of the scalar element pattern response. This elevation scanning capability is exploited by phased-array signal processing circuitry 470 to fill in the gaps in coverage that would otherwise result, thereby truly providing electronic 3D volumetric data acquisition.

Pursuant to the example in the preceding paragraph, phased-array signal processing circuitry 470 is programmed to provide full, electronic 3D volumetric data acquisition. Any given transducer substrate can be scanned upwards or downwards exemplarily 0.1 radians in the elevation dimension by applying appropriately computed time delays to the seven elements in the width dimension. It will now be explained how this phased array scanning accommodates or compensates for the 9 mm gap in the width dimension contained between two adjacent substrates. At a depth of 5 cm, the beam scanned upwards from the lower substrate will intersect the beam scanned downwards by the upper substrate, thereby providing full coverage (i.e. completely filling in the gap) for depths greater than five centimeters. The same coordinated approach is used between other adjacent substrates to acquire the complete 3D volume for depths greater than 5 cm. Gaps for nearer-in depths are filled by treating the collection of scalar elements contained in the width dimension of the data gathering aperture (at a given location along the length of the data gathering aperture) as a single array, and using appropriate subapertures depending on the width interval being interrogated. One can appreciate that by designing a subaperture so that its phase centre is sufficiently close to the gap in question will insure that the gap can be filled in (i.e. interrogated by the subaperture). The subaperture approach also has the advantage that an instantaneous aperture larger than the width dimension (1 cm in this example) of each substrate can be used to increase the elevation resolution, which is highly desirable in many applications.

While the above presentation illustrates the practical electronic 3D volumetric data acquisition capability of phased-array signal processing, the particular scanning methods illustrated are not intended to limit the scope of the 2D electronic scanning capabilities of platen 468. For example, one could view all of the transducer elements provided within a data gathering aperture as addressable elements of a 2D phased array. Therefore, joint 2D phased array scanning can be performed rather than the factored azimuth and elevation scanning approaches discussed throughout. Clearly, these more general approaches are contemplated as within the scope of operation of phased-array signal processing circuitry 470.

Additional, unique, and unconventional features of the phased-array signal processing circuitry 470 are provided as described hereinafter (with reference to the example just previously described), when the acquisition time of the 3D volumetric data must be minimized. It is well understood that to image a moving organ such as the heart, the total acquisition time should be on the order of 30 ms or less. Considering a depth of 15 cm, the two-way, time-of-flight of each transmitted pulse is approximately 0.2 ms. For the transducer array of the above example with 100 elements in the length dimension, the azimuth acquisition time (assuming 100 vectors and one pulse per vector) is 20 ms. If multiple receive beams (vectors) are formed from each transmit pulse (a factor of 3 is common in practice), then the azimuth acquisition time can be reduced to about 7 ms. However, if a linear transducer array (i.e. a linear data gathering aperture) is formed containing say 1000 elements along the length dimension, at least 70 ms is then needed to acquire the 2D image slice. In this case, unconventional electronic scanning (as described hereinafter) is needed to reduce the acquisition time. The situation is compounded further when 3D volumetric data acquisition is performed. If a full 2D array containing 100 elements closely spaced in each of the length and width dimensions is used, then about 33 pulses (with the factor of 3 multiplexing accounted for) are needed for elevation scanning, for each azimuth beam. As a result, the acquisition time increases proportionately to approximately 220 ms. If multiple pulses are needed for each vector for multiple depths of focus, the acquisition time further increases proportionately. For platen 468 utilizing 1.5D array substrates, on the order of 10 elevation beams (i.e., pulses assuming 1 pulse per beam) are needed to fill the 1 cm gap (each slice is about 1 mm thick in the elevation dimension) between adjacent array substrates. Assuming that the adjacent 1.5D array substrates are operated simultaneously (or near simultaneously), then 330 pulses are needed for 3D volumetric scanning, requiring an acquisition time of 66 ms. Again, multiple depths of focus will multiply this acquisition time.

The discussion in the preceding paragraph illustrates the need to reduce acquisition time for full 2D scanning arrays, and for platen 468 of the above example, utilizing 1.5D array substrates, in certain applications. Conventional azimuth electronic scanning (and by extension, elevation scanning) transmits pulses sequentially; that is, the first pulse is transmitted (i.e. first pressure wave) and received (i.e. second pressure wave) prior to transmitting the next pulse. In order to reduce the total acquisition time for 3D volumetric data acquisition (which includes 2D acquisition as a special case as described earlier), several pulses are to be transmitted in rapid succession (i.e., one following immediately after the preceding pulse is launched) so that several pulses are in-flight simultaneously. Each of the in-flight pulses is transmitted with a different transmit beam separated significantly (i.e., in azimuth and/or elevation) from the other transmit beams associated with the other in-flight pulses. This beam-pulse interleaving technique reduces (to acceptable levels) the co-beam-pulse interference caused by the other in-flight pulse returns when forming the receive beams (i.e., vectors) associated with a given in-flight pulse's returns. Furthermore, the beam-pulse interleaving technique causes the acquisition time to be reduced by a factor equal to the average number of in-flight-pulses. The selection of beam-pulse sets for use with this beam-pulse interleaving technique need not be regular, and can be optimized both in terms of the number of beams per set and their locations (in azimuth, elevation or both) so as to meet the acquisition time requirements while maintaining specifications on co-beam-pulse interference rejection. The costs associated with employing the beam-pulse interleaving technique are an increased minimum depth (range) of operation which corresponds to the total time taken to transmit the in-flight pulses in rapid succession (which is small in practice), and increased computational requirements to form the multiple receive beams (vectors) in parallel, in order to maintain real-time performance.

A variation to the beam pulse interleaving technique described above would cause successive in-flight pulses to be launched each using a different waveform code (i.e., waveform pulse interleaving) which varies any or all of the amplitude, frequency or phase of the transmitted pulse rather than (or in addition to) directing each pulse to different spatial directions or beams. In this way, the co-waveform pulse interference can be reduced to acceptable levels, thereby separating the interfering returns from different in-flight pulses. Such approaches are likely to be more suitable for narrow band systems than for wide band systems.

An alternative to the rapid, successive transmission of in-flight pulses each directed using a different transmit beam is to form a composite transmit beam pattern representing the superposition of the individual beam patterns associated with the in-flight pulses, and transmitting a single pulse. This alternative approach, however, can suffer from reduced power directed to the associated beam directions, and hence reduced power on receive.

It is emphasized here that the aforementioned beam-pulse interleaving technique is applicable to both full 2D scanning arrays as well as those based on 1.5D technology as described in the instant disclosure. The scanning functionality provided by the beam-pulse interleaving technique forms part of the phased-array signal processing circuitry 470.

Phased-array signal processing circuitry 470, like acquisition controller 442 as a whole and other components shown in FIG. 29, is realizable in the form of digital processor circuits modified by programming to operate transducer packages or apertures 466 as a phased array. Thus, phased-array signal processing circuitry 470 and the signal processing and control elements of FIG. 29 are all realizable by a properly programmed digital computer. It should be noted that the terminology "phased array" used throughout this application is intended to be applicable to both narrow-band and wide-band waveforms, although, strictly speaking, the term originates from systems employing narrow-band waveforms where the phase of a signal is varied to effectuate scanning. It is understood that for wide-band waveforms such as those often employed in ultrasound systems, it is the time delay of the signals (rather than the phase) that must be varied across a given data gathering aperture in order to effectuate electronic scanning. In the instant disclosure, the term "delay" is intended to cover both a phase variation and a time delay as applicable in the use of wide-band waveforms.

It is of interest that imaging occurs in the far field of each individual transducer element 438 and in the near field of package or array aperture 436. The near-field variation of a wavefront across an aperture 438 is quadratic. As a result, focusing an array aperture in a phased-array process is achieved by computing and applying the appropriate quadratic time delays, for the location in question that is being focused. A variety of approaches are known to those skilled in the art to optimize this process for a given application.

Of course, the physics of ultrasound are well documented and understood. Software for any of the ultrasonic imaging systems herein entails a straightforward application of the appropriate wave equations. See, for instance, *Principles of Aperture and Array System Design*, B. D. Steinberg, John Wiley, 1976, and *Ultrasonic Imaging Using Arrays*, Proc. IEEE, Vol. 67, No. 4, April 1979, pp 484-495.

Although the invention has been described in terms of particular embodiments and applications, one of ordinary skill in the art, in light of this teaching, can generate additional embodiments and modifications without departing from the spirit of or exceeding the scope of the claimed invention. It is to be understood, for instance, that the various processing functions (e.g., aperture formation, coherent aperture combining, self-cohering algorithm calculation, etc.) may be performed by a specially programmed general purpose computer as disclosed herein or, alternatively, by hard wired circuits. Hard wiring may be especially advantageous for various preprocessing and calibration or position determination computations.

Moreover, it is to be noted that multiple images may be provided on a single video screen, pursuant to conventional windows-type overlay techniques. Thus, one window or video image may show an organ from one point of view or angle, while another window on the same screen may show the same organ from a different vantage point. Alternatively, one window may show a first organ, while another window displays one or more organs underlying the first organ. In this case, the underlying organs may be shown in phantom line in the first window, while the overlying organs is shown in phantom lines in the second window. Of course, all such operating modes apply to multiple video screens as well as to a single screen. Thus, one screen may display an overlying organ from one angle, while an adjacent organ displays an underlying organ from a different angle. A display window on a video screen of the present invention may be used alternatively for the display of textual information pertaining to the tissues and organs displayed in other video windows. Such information may include diagnostic information determined by the analyzing computer.

It is to be further noted that the 1.5D transducer arrays discussed herein could be replaced by so-called 1.75D arrays. Accordingly, the term "1.5D transducer array" as used herein should be understood to encompass 1.75D transducer arrays, as well.

Accordingly, it is to be understood that the drawings and descriptions herein are profered by way of example to facilitate comprehension of the invention and should not be construed to limit the scope thereof.

What is claimed is:

1. A medical method comprising:
   providing a carrier holding a multiplicity of electromechanical transducers defining respective data gathering apertures;
   placing said carrier and a patient adjacent to one another so that said transducers are disposed in effective pressure-wave-transmitting contact with the patient;
   supplying a first plurality of said transducers with electrical signals of at least one pre-established ultrasonic frequency to produce first pressure waves in the patient;
   receiving, via a second plurality of said transducers, second pressure waves produced at internal tissue structures of the patient in response to said first pressure waves; and
   performing electronic 3D volumetric data acquisition and imaging of said internal tissue structures by analyzing signals generated by said second plurality of said transducers in response to said second pressure waves,
   the analyzing of signals generated by said second plurality of said transducers including coherently combining structural data from the respective data-gathering apertures,
   said carrier including a plurality of rigid substrates containing said data-gathering apertures, the coherently combining of structural data from the respective data-gathering apertures including determining relative positions and orientations of said substrates relative to one another,
   the determining of relative positions and orientations of said substrates including executing computations according to a self-cohering algorithm.

2. The method defined in claim 1 wherein each of said substrates is provided with a plurality of point scatterers, the determining of relative positions and orientations of said substrates including periodically scanning said point scatterers with ultrasonic pressure waves and calculating instantaneous positions of said point scatterers.

3. The method defined in claim 2 wherein the determining of relative positions and orientations of said carriers includes executing computations according to a self-cohering algorithm.

4. The method defined in claim 1 wherein the determining of relative positions and orientations of said carriers includes periodically energizing at some of said transducers with at least one predetermined electrical frequency and calculating instantaneous positions of the transducers so energized.

5. A medical scanning method comprising:
   providing a plurality of electromechanical sensors disposed in data-gathering arrays or apertures on respective rigid substrates mounted to a flexible carrier;
   disposing said carrier in relation to a patient;
   after the disposing of said carrier, activating said sensors to effectuate a solely electronic ultrasonic-wave scan of internal organic structures of the patient resulting in encoded three-dimensional structural data pertaining to the internal organic structures, the activating of said sensors including exciting said sensors to define said data-gathering arrays or apertures;
   the activating of said sensors including generating a plurality of tissue-scanning beams via respective ones of said data-gathering arrays or apertures to capture or produce structural data pertaining to said internal organic structures and combining the structural data from said data-gathering arrays or apertures; and operating on the data from said sensors to produce an electronically encoded three-dimensional model or analog of said internal organic structures.

6. The method defined in claim 5 wherein said three dimensional model is produced from said data alone.

7. The method defined in claim 6, further comprising generating an image of at least one of said internal structures from said model.

* * * * *